(12) United States Patent
Berentsveig et al.

(10) Patent No.: US 9,241,491 B2
(45) Date of Patent: Jan. 26, 2016

(54) AEROSOL

(71) Applicant: SABAN VENTURES PTY LIMITED, Alexandria (AU)

(72) Inventors: Vladimir Berentsveig, Alexandria (AU); Gary Erickson, Alexandria (AU); Ron Weinberger, Alexandria (AU)

(73) Assignee: Saban Ventures Pty Limited, Lane Cove, New South Wales (AU)

( * ) Notice: Subject to any disclaimer, the term of this patent is extended or adjusted under 35 U.S.C. 154(b) by 96 days.

(21) Appl. No.: 14/085,924

(22) Filed: Nov. 21, 2013

(65) Prior Publication Data

US 2014/0154135 A1    Jun. 5, 2014

Related U.S. Application Data

(62) Division of application No. 11/997,855, filed as application No. PCT/AU2006/001113 on Aug. 4, 2006, now Pat. No. 8,591,808.

(30) Foreign Application Priority Data

| Aug. 4, 2005 | (AU) | ................................. | 2005904181 |
| Aug. 4, 2005 | (AU) | ................................. | 2005904196 |
| Aug. 4, 2005 | (AU) | ................................. | 2005904198 |
| Feb. 15, 2006 | (AU) | ................................. | 2006900748 |

(51) Int. Cl.
*A61L 2/00* (2006.01)
*A61L 9/00* (2006.01)
(Continued)

(52) U.S. Cl.
CPC ................ *A01N 59/00* (2013.01); *A01N 25/06* (2013.01); *A61L 2/06* (2013.01); *A61L 2/16* (2013.01);
(Continued)

(58) Field of Classification Search
CPC ............ A61L 2/00; A61L 2/186; A61L 2/208

USPC ............ 422/1, 20, 28, 32, 125, 298, 305–306
See application file for complete search history.

(56) References Cited

U.S. PATENT DOCUMENTS

| 3,476,506 A | 11/1969 | Anderson et al. |
| 3,481,689 A | 12/1969 | Rosdahl et al. |

(Continued)

FOREIGN PATENT DOCUMENTS

| EP | 0679407 A2 | 11/1995 |
| GB | 663720 | 12/1951 |

(Continued)

OTHER PUBLICATIONS

McDonnell, G., et al., "Antiseptics and Disinfectants: Activity, Action, and Resistance," 1999, Clin Microbiol Rev, 12/1:147-179.

(Continued)

*Primary Examiner* — Monzer R Chorbaji
(74) *Attorney, Agent, or Firm* — Senniger Powers LLP

(57) ABSTRACT

A nebulant suitable for sterilization comprising finely divided liquid droplets suspended in a gas, said droplets including a solute, which is advantageously hydrogen peroxide and a solvent, for example water, wherein the droplets have a concentration of greater than 60 wt % of solute and an average diameter of less than 1.0 micron, preferably less than 0.8 microns. Sterilization using the nebulant may be carried out in suitably adapted apparatus by nebulizing a solution comprising a sterilizing agent in a solvent to form a nebulant of finely divided particles of the solution in a gas stream, said solution including a solvent having a lower boiling point than the sterilizing agent; subjecting the nebulant to energy of a kind and for a duration sufficient to vaporize solvent in preference to sterilizing agent, whereby to increase the concentration of the agent in the nebulant particles; removing the solvent vaporized from the gas stream at or above atmospheric pressure and, if necessary, cooling the nebulant to below 70° C.; and exposing a surface to be sterilized to the nebulant of concentrated sterilizing agent for a time sufficient to sterilize the surface.

20 Claims, 26 Drawing Sheets

(51) Int. Cl.
  *A62B 7/08* (2006.01)
  *A01N 59/00* (2006.01)
  *A01N 25/06* (2006.01)
  *A61L 2/06* (2006.01)
  *A61L 2/20* (2006.01)
  *A61L 2/22* (2006.01)
  *A61L 2/24* (2006.01)
  *C01B 15/013* (2006.01)
  *A61L 2/16* (2006.01)

(52) U.S. Cl.
  CPC . *A61L 2/20* (2013.01); *A61L 2/208* (2013.01); *A61L 2/22* (2013.01); *A61L 2/24* (2013.01); *C01B 15/013* (2013.01); *A61L 2202/24* (2013.01)

(56) References Cited

U.S. PATENT DOCUMENTS

| | | | |
|---|---|---|---|
| 3,950,247 | A | 4/1976 | Chiang et al. |
| 4,022,324 | A | 5/1977 | Schuster |
| 4,191,543 | A | 3/1980 | Peters |
| 4,296,068 | A | 10/1981 | Hoshino |
| 4,366,125 | A | 12/1982 | Kodera et al. |
| 4,680,163 | A | 7/1987 | Blidschun et al. |
| 4,718,985 | A | 1/1988 | Kjellander |
| 4,744,951 | A | 5/1988 | Cummings et al. |
| 4,958,529 | A | 9/1990 | Vestal |
| 4,978,430 | A | 12/1990 | Nakagawa et al. |
| 5,454,274 | A | 10/1995 | Zhu |
| 5,611,842 | A | 3/1997 | Friesen et al. |
| 5,843,209 | A | 12/1998 | Ray et al. |
| 5,851,485 | A | 12/1998 | Lin et al. |
| 6,066,294 | A | 5/2000 | Lin et al. |
| 6,325,972 | B1 | 12/2001 | Jacobs et al. |
| 6,379,616 | B1 | 4/2002 | Sheiman |
| 6,500,465 | B1 | 12/2002 | Ronlan |
| 6,656,426 | B1 | 12/2003 | Wang et al. |
| 6,977,061 | B2 | 12/2005 | Lin et al. |
| 7,014,813 | B1 | 3/2006 | Watling et al. |
| 7,122,166 | B2 | 10/2006 | Parrish |
| 7,326,382 | B2 | 2/2008 | Adiga et al. |
| 2002/0119075 | A1 | 8/2002 | Jacobs et al. |
| 2002/0192110 | A1* | 12/2002 | Garlick .................. 422/37 |
| 2003/0143110 | A1 | 7/2003 | Kritzler et al. |
| 2003/0183576 | A1 | 10/2003 | Ohara et al. |
| 2003/0192799 | A1 | 10/2003 | Addy et al. |
| 2004/0022673 | A1 | 2/2004 | Protic |
| 2004/0062692 | A1 | 4/2004 | Lin et al. |
| 2005/0084415 | A1* | 4/2005 | McVey et al. .................. 422/28 |
| 2005/0252856 | A1 | 11/2005 | Parrish |

FOREIGN PATENT DOCUMENTS

| | | |
|---|---|---|
| GB | 2346095 A | 8/2000 |
| JP | 55-137007 | 10/1980 |
| JP | S60220067 | 2/1985 |
| JP | 60-206408 | 10/1985 |
| JP | S60220067 A | 11/1985 |
| JP | 63-175602 | 7/1988 |
| JP | 02-273518 | 11/1990 |
| JP | 10-284458 | 10/1998 |
| JP | H11-47244 A | 2/1999 |
| JP | 2003-095617 | 4/2003 |
| JP | 2003-180802 | 7/2003 |
| JP | 2004-267755 | 9/2004 |
| JP | 2006519780 A | 8/2006 |
| WO | 9111374 A2 | 8/1991 |
| WO | 9602316 A1 | 2/1996 |
| WO | 9966961 A1 | 12/1999 |
| WO | 02056988 A2 | 7/2002 |
| WO | 2004073827 A1 | 9/2004 |

OTHER PUBLICATIONS

Content and Format of Premarket Notification [510(k)] Submissions for Liquid Chemical Sterilants/High Level Disinfectants, Jan. 3, 2000, Guidance for Industry and FDA Reviewers, CDRH, 59 pages.
English translation of Office Action issued in Japanese Patent Application No. 2008-524316, mailed Nov. 29, 2011, provides brief description of JP S60220067 for which no English translation is available. 5 pages.
"Explanation of HMIS Ratings," obtained from http://www.paint.org/component/docman/cat_view/49-hmis.html on Feb. 10, 2012, 2 pages.
Material Safety Data Sheet, Peracetic Acid, 35% MSDS, Sciencelab.com, created Oct. 10, 2005, Updated Nov. 1, 2010, 7 pages.
Material Safety Data Sheet, Hydrogen Peroxide Solutions Greater Than 60%, FMC MSDS Ref. No. 7722-84-1-5, Date Approved May 21, 2011, Revision No. 12, 11 pages.
Material Safety Data Sheet, Ethanol Solution, Sigma-Aldrich Corporation, Version 3.1, Revised Jul. 12, 2011, Printed Feb. 10, 2012, 7 pages.
International Search Report, PCT/AU2006/001113, dated Sep. 13, 2006, 3 pages.
International Preliminary Examination Report, PCT/AU2006/001113, dated Jul. 25, 2007, 3 pages.
Abstract of JP 2002-201004, Toyota Motor Corp., Jul. 16, 2002, 1 page.

* cited by examiner

Water content and relative humidity during disinfection cycle.

Relationship between mated surface sterilization and humidity

FIGURE 11

Relationship of biocidal efficacy to $H_2O_2$ delivery rate and aerosol velocity

Temperature 45oC    Relative humidity 30-50%

FIGURE 12

Relationship between biocidal efficacy, $H_2O_2$ delivery rate and nebulizer power supply.

Temperature 45°C   Relative humidity 30-50%

Figure 16

| Table 1: Max. peroxide vapour concentration using initial 35% $H_2O_2$ solution (mg/m³) | | | | |
|---|---|---|---|---|
| Temperature (°C) | 10% RH | 20% RH | 40% RH | 80% RH |
| 20 | 0.97 | 0.85 | 0.62 | 0.14 |
| 40 | 4.13 | 2.59 | 2.66 | 0.63 |
| 60 | 14.4 | 12.60 | 9.1 | 2.31 |

Figure 17

| Table 2: Water content and relative humidity during disinfection cycle of example 2 |||||
|---|---|---|---|
| Delivery rate: 10mg/L/min<br>Amount of applied energy: 1.5KJ/min<br>Initial $H_2O_2$ solution 35% ||||
| Disinfection time, min | Calculated RH,% (no water removal) | Measured RH,% | Removed water,g/m$^3$ |
| 0  | 20 | 20 | 0 |
| 1  | 24 | 22 | 1.5 |
| 2  | 41 | 36 | 3.0 |
| 3  | 53 | 45 | 4.5 |
| 4  | 59 | 48 | 6.0 |
| 5  | 63 | 49 | 7.5 |
| 6  | 67 | 50 | 9.0 |
| 7  | 71 | 51 | 11.0 |
| 8  | 75 | 52 | 12.0 |
| 9  | 79 | 53 | 14.0 |
| 10 | 83 | 54 | 15.0 |
| 11 | 86 | 54 | 17.0 |
| 12 | 89 | 54 | 18.0 |
| 13 | 92 | 54 | 20.0 |
| 14 | 95 | 54 | 21.0 |
| 15 | 99 | 55 | 23.0 |

Figure 18

| Table 3: Endoscopic lumen disinfection by method of invention . |||||||
|---|---|---|---|---|---|
| Test organism: Bacillus stearothermophilus<br>Concentration of the initial $H_2O_2$ solution 35%.<br>Temperature in the chamber 43°C,<br>Sterilization time 10 min |||||||
| Endoscope type | Channel internal diameter | Channel length | $H_2O_2$ delivery rate, mg/L/min | Relative humidity' % | Reduction of spore population by a factor of Log 6, positive/tested |
| Biopsy channel ||||||
| Colonoscope Pentax EC#AO1216 | 3.8 mm | 3.2m | 8.0 | 40-60 | 5/5 |
| Colonoscope Pentax EC 380IF#AO1216 | 3.8 mm | 3.5m | 9.0 | 40-60 | 5/5 |
| Gastroscope Pentax ECEC29OP | 2.8 mm | 2.5m | 8.5 | 40-60 | 5/5 |
| Air and water channel ||||||
| Colonoscope Pentax EC#AO1216 | 1.8 mm - air<br>1.6 mm - water | 3.2m | 7.6 | 40-60 | 5/5 |
| Colonoscope Pentax EC 380IF#AO1216 | | 3.5m | 8.0 | 40-60 | 3/3 |
| Gastroscope Pentax ECEC29OP | | 2.5m | 7.8 | 40-60 | 2/2 |

Figure 19

| Table 4: Disinfection of mated surfaces by method of the invention |||||
|---|---|---|---|---|
| Test organism: Bacillus stearothermophilus<br>Concentration of the initial $H_2O_2$ solution 35%.<br>Temperature in the system 45°C |||||
| Type of carriers | Sterilization time | $H_2O_2$ delivery rate | Relative humidity, % | Reduction of spore population by a factor of Log 6,<br><br>positive/tested |
| Stainless Steel washers (3mm depth) | 10 min | 9.0 mg/L/min | 30-50 % | 10/10 |
| | 15 min | 8.5 mg/L/min | 30-50 % | 60/60 |

Figure 20

| Table 5: Disinfection efficacy on mated surfaces with varying surface area |||||||||
|---|---|---|---|---|---|---|---|
| Test organism: Bacillus stearothermophilus<br>Concentration of the initial $H_2O_2$ solution 35%.<br>Temperature in the system 45°C |||||||||
| Type of carriers | Sterilization time | $H_2O_2$ delivery rate, mg/L/min | Relative humidity % | Reduction of spore population by a factor of Log 6, positive/tested ||||
| Mated surface depth | | | | 85 $mm^2$ | 200 $mm^2$ | 300 $mm^2$ | 450 $mm^2$ |
| Stainless Steel washers | 10 min<br>15 min | 8.8<br>13.0 | 35-60% | 2/2<br>2/2 | 2/2<br>2/2 | 2/2<br>2/2 | 2/2<br>2/2 |

Figure 21

| Table 6: Sterilisation efficacy on inoculum condition on open surfaces by method of invention |||||||
|---|---|---|---|---|---|---|
| Test organism: Bacillus stearothermophilus<br>Concentration of the initial $H_2O_2$ solution 35%.<br>Temperature in the cassette 45°C |||||||
| Type of carriers | Sterilization time | $H_2O_2$ delivery rate | Relative humidity, % | Reduction of spore population by a factor of Log 6, positive/tested |||
| Inoculum condition |  |  |  | dry | wet | fresh |
| Stainless Steel washers | 3 min<br>5 min<br>9 min | 7.8mg/L/min | 35-50% | 2/2<br>2/2<br>2/2 | 2/2<br>2/2<br>2/2 | 2/2<br>2/2<br>2/2 |

Figure 22

| Table 7: Sterilisation with respect to time on open surfaces of different materials by method of the invention. | | | | |
|---|---|---|---|---|
| Test organism: Bacillus stearothermophilus<br>Concentration of the initial $H_2O_2$ solution 35%.<br>Size of carriers : 400 mm$^2$ and 800mm$^2$<br>$H_2O_2$ delivery rate: 9.9mg/L/min | | | | |
| Temperature in the chamber 45°C | | | | |
| Type of carriers | Relative humidity, % | Reduction of spore population by a factor of Log 6, positive/tested | | |
| Sterilization time | | 2 min | 5 min | 10 min |
| Stainless Steel cylinders<br>Penicylinders<br><br>flat surfaces<br>Stainless Still<br>Polyurethane<br>Nylon (polyamide)<br>Polyvinylchloride<br>Polyethylene<br>Teflon (polytetrafluoroethylene)<br>Silicone rubber<br>Neoprene rubber | 30-50% | -<br>-<br><br>5/5<br>0/4<br>0/4<br>5/5<br>5/5<br>5/5<br>0/4<br>0/4 | -<br>-<br><br>5/5<br>0/4<br>0/4<br>5/5<br>5/5<br>5/5<br>4/4<br>4/4 | 3/3<br>3/3<br><br>5/5<br>4/4<br>5/5<br>5/5<br>5/5<br>5/5<br>4/4<br>4/4 |
| Temperature in the chamber 25°C<br>$H_2O_2$ delivery rate: 9.9 mg/L/min | | | | |
| Sterilization time | | 2 min | 5 min | 10 min |
| Stainless Steel flat surfaces | 35-60% | 4/6 | 6/6 | 6/6 |

Figure 23

| | | Open surfaces | | | | Mated surfaces | |
|---|---|---|---|---|---|---|---|
| | | | | | Total | | |
| | | Spores | Spores | | amount of | Spores | |
| | | before | after | Time of | peroxide | after | Time of |
| EXP | Nebulant | treatment, | treatment, | treatment | on the | treatment, | treatment |
| | | cfu/mL | cfu/mL | | surface | cfu/mL | |
| A | 10% $H_2O_2$ Not heated, 20 °C, (RH% = 90%) | 1x $10^6$ | 0 | 1 min | 5-7 µg/$cm^2$ | 0 | >60 min |
| B | 35% $H_2O_2$ Heated 40°C, no water vapour removal (RH 92%) | 1x $10^6$ | 0 | 1 min | 3 µg/$cm^2$ | 0 | >25 min |
| C | 35% $H_2O_2$ Heated 40°C, water removed (RH55%) | 1x $10^6$ | 0 | 1 min | 0.3 µg/$cm^2$ | 0 | <10 min |
| D | 50% $H_2O_2$ Heated 40°C, no water removed (RH 81%) | 1x $10^6$ | 0 | 1 min | 6.6 µg/$cm^2$ | 0 | 20 min |

TABLE 8

Figure 24

| Table 9: Comparison of efficacy of nano nebulant with vapour |||||
|---|---|---|---|
| Type of carriers (open surfaces) | Sterilization environment | Spore population before treatment, cfu/mL | Spore population after treatment, cfu/mL |
| Stainless steel washers | nano nebulant | $1\times10^6$ | 0 |
| Stainless steel washers | Vapour (1200ppm) | $1\times10^6$ | $1\times10^2$ |
| Penicylinder | nano nebulant | $1\times10^6$ | 0 |
| Penicylinder | Vapour (1200ppm) | $1\times10^6$ | $3\times10^3$ |

Figure 25

| Table 10: Relationship of $H_2O_2$ delivery rate to air flow velocity, nebulizer power supply, nebulizer duty cycle and % of initial $H_2O_2$ solution. | | | | |
|---|---|---|---|---|
| | Parameters | $H_2O_2$ delivery rate, mg/L/min | Relative humidity, % | Log reduction of spore population |
| Aerosol velocity | 0.0 m/sec<br>0.5 m/sec<br>0.95 m/sec<br>1.5 m/sec<br>2.0 m/sec | 3.4<br>5.7<br>7.2<br>9.1<br>9.2 | 40-50 | 0<br>0.6<br>5.7<br>6.3<br>6.3 |
| Power supply | 16 W<br>20 W<br>30 W | 2.0<br>3.7<br>7.9 | 30-50 | 4.7<br>6.3<br>6.3 |
| Nebulizer duty cycle | 5 sec/min<br>10 sec/min<br>2 sec/min<br>30 sec/min<br>40 sec/min | 1.6<br>3.3<br>7.8<br>15.6<br>19.1 | 30-60 | 5.1<br>5.5<br>6.3<br>6.3<br>6.3 |
| Initial $H_2O_2$ solution concentration | 3 %<br>10 %<br>20 %<br>35 %<br>50 % | 0.9<br>3.4<br>5.1<br>7.6<br>9.8 | 30-60 | 1.3<br>2.7<br>5.8<br>6.3<br>6.3 |

Figure 26

TABLE 11

Effect of duty cycle on sterilization efficacy and residuals

Conditions in cassette:

| | |
|---|---|
| Initial Hydrogen Peroxide concentration: | 35°C |
| Heater temperature at outlet: | 10-115°C |
| Cold trap temperature: | inlet 26°C ; outlet 17°C |
| Nebuliser power : | 10w |
| Aerosol flow rate | 2m/s |
| Duty cycles: | A. 2 secs on / 10secs off |
| | B. 5 secs on / 15secs off |
| | C. 10 secs on and 10 secs off |

Duty cycle run for 2 mins; then cassette sealed off for 8 mins (total 10mins)

| Sterilisation time, min (cycle ON/OFF) | Temp. in chamber °C | Temp. in cassette, °C | Max.$H_2O_2$ vapour conc. ppm | Final relative humidity in the cassette % | Reduction of the bio-burden by a factor of Log 6 |
|---|---|---|---|---|---|
| 10(2&18) | 35 | 33 | 1050 | 50 | 6.3 |
| 10(5&15) | 35 | 33 | 700 | 58 | 6.3 |
| 10(10&10) | 35 | 33 | 425 | 63 | 6.3 |

AEROSOL

REFERENCE TO RELATED APPLICATIONS

This application is a division of U.S. patent application Ser. No. 11/997,855, which is the U.S. National Stage Application of International Application No. PCT/AU2006/00113, filed Aug. 4, 2006, and is now U.S. Pat. No. 8,591,808, and claims the benefit of Australia Patent Application No. 2005904181, filed Aug. 4, 2005, Australian Patent Application No. 2005904196, filed Aug. 4, 2005, Australian Patent Application No. 2005904198, filed Aug. 4, 2005, and Australian Patent Application No. 2006900748, filed Feb. 15, 2006, the entire disclosures of which are incorporated herein by reference.

FIELD OF INVENTION

This invention relates to an improved method for disinfection or sterilization of medical instruments.

The requirements for sterilizing medical instruments are exacting and the invention will be herein described with particular reference to that application, but it will be understood that the invention is also applicable for sterilizing other articles or apparatus in need of disinfection or sterilization such as used in dentistry, hairdressing, and the like. It will also be understood that while the invention is capable of meeting the requirements for sterilizing medical instruments it can also be used for less demanding tasks such as disinfection. The invention also relates to novel apparatus for use in the method, and to compositions of use in conducting the method.

BACKGROUND OF THE INVENTION

Prior to the late 1960's medical instruments were sterilized by autoclaving, by liquid sterilization systems such as glutaraldehyde, or by use of ethylene oxide. In the late sixties and early seventies sterilization systems involving aerosols of less obnoxious sterilants were proposed, and machines employing aerosol systems were developed for use in the packaging industry. However aerosols were not able to meet the requirements for sterilizing medical instruments and particularly were unsuccessful in treating lumens and occluded or mated surfaces. Consequently aerosol systems soon gave way to vapour and plasma based systems which were shown to be faster and more effective for sterilizing mated surfaces, lumens and occluded surfaces, although liquid phase systems continued to be used.

Chemical sterilizing systems may thus be broadly classified into three categories:
(1) Liquid systems employing a biocidal agent in the liquid phase,
(2) Aerosol systems in which a biocidal agent in a liquid phase is employed as a finely divided suspension of droplets in a gas, and
(3) Vapour systems employing the agent in a gaseous, plasma, or vapour phase, The third (vapour) category may be further subdivided into systems employing the gas or vapour at atmospheric pressure or above, and those (including gas plasmas) which operate at sub-atmospheric pressure.

Each of the above categories of process has had disadvantages for treating medical instruments. The inadequacies of known techniques for sterilization become particularly evident when attempts are made to sterilize an endoscope. Endoscopes have narrow lumens of small diameter, for example 1 mm, and may be more than 2.0 meters in length. Many of their parts such as the control head include mated surfaces, or occluded surfaces. Their construction incorporates heat sensitive materials and they should not be heated above about 70° C. It would be desirable to be able to sterilize an endoscope, and have it immediately ready for use (i.e. sterile, dry, and at below 45° C.), in the time that it takes to conduct an endoscopic procedure, say within about 20 minutes. Because endoscopes cannot be sterilized in the time that it takes to perform a procedure, a large amount of capital is tied up in additional endoscopes consequently required.

Prior to the present invention it has not been possible to present a sterilised, dry, safe endoscope, ready for reuse in less than about 20 minutes. Also prior art liquid processes have either used external rinse water, with an attendant risk of infection, or require sterile rinse water, while vapour systems require a vacuum system with attendant disadvantages.

Similar problems to those experienced with endoscopes arise when attempting to sterilize mated surfaces, such as occur in many medical instruments, for example those having threaded parts, and also at the point of support of instruments in a sterilization chamber. Unless the sterilizing agent can penetrate mated surfaces, that part of the surface which is supported in the sterilizer may harbour micro-organisms and the instrument will not be sterile. This can only be avoided by shifting the points of support but at the cost of doubling the treatment time and added complexity.

Although the present invention is an improved aerosol system, the process has advantages over prior art liquid and prior art vapour sterilization systems and consequently each of those systems will also be briefly reviewed.

Liquid Sterilizing Agents

Although liquid sterilizing agents have been used for many years for sterilizing articles such as medical and dental instruments, packaging, and the like, and not withstanding research over many decades to solve the problems involved, the use of bulk liquid sterilants still suffers from a number of disadvantages. It is important that a disinfection process has the ability to kill all micro-organisms, and not merely one class, as is the case with many liquid agents. A major disadvantage of liquid sterilizing systems such as are currently used for sterilizing medical instruments is that they employ particularly hazardous chemicals the use of which are increasingly causing occupational health concerns around the world. Other disadvantages include long sterilization cycles, high materials costs, as well as costs associated with the time and energy required to subsequently remove liquid from an article and/or to dry it after sterilization and prior to use. In addition to requiring long treatment times and drying times, many liquid sterilants are corrosive or otherwise materials incompatible with endoscope construction materials. If excessive residual sterilizing agent is left on the instrument, there may be a risk of an anaphylactic reaction when the instrument is introduced into a body cavity, and to avoid that possibility residual sterilizing agent must be rinsed off. The use of rinse water in turn introduces a risk of infection but is a lesser evil than the possibility of cytotoxic reaction.

Also the requirement for rinse water imposes a need for a water supply and drainage system which is a major disadvantage in some locations. Moreover, the need for plumbing prevents such apparatus from being portable or easily relocated.

Gasses and Vaporized Sterilizing Agents, at Atmospheric Pressure or Above.

Traditionally, vapour sterilization of medical instruments was performed with steam (water vapour), usually in autoclaves at high temperature and pressure. More recently gases such as ethylene oxide have been used at temperatures around 55° C. (e.g. U.S. Pat. No. 4,410,492), but in view of both occupational health and environmental concerns, the use of such highly toxic gases has been largely discontinued in many countries and is being rapidly discontinued in others around the world.

The use of hydrogen peroxide vapours was pioneered in the packaging industry, where it has been practiced to "gasify" peroxides for use as a sterilizing agent. Hydrogen peroxide is considered harmless and non corrosive in comparison with ethylene oxide, chlorine, ozone and other gasses employed as sterilants. Hydrogen peroxide can be vaporized at atmospheric pressure by feeding droplets of 1-3 mm diameter onto a surface heated at 140-180° C. whereby the liquid is vaporized and then swept by a carrier gas to be directed at a surface to be sterilized (eg U.S. Pat. No. 4,797,255, Hatanaka) or by injecting the droplets into a pre-heated gas stream at above 140° C.

Hydrogen peroxide boils at 151.4° C. at 760 mm. FIG. 1 taken from U.S. Pat. No. 4,797,255 shows (curve A) how the boiling point at atmospheric pressure of a water/peroxide mixture changes with concentration and (curve B) how the gas composition changes. As is shown, pure water boils at 100° C. at atmospheric pressure. It is evident from FIG. 1 that the concentration of hydrogen peroxide in the vapour at below 100° C. is negligible at atmospheric pressure.

In peroxide vapour processes at atmospheric pressure, it is essential that the hydrogen peroxide vapour be kept at substantially above its Dew Point (i.e. below its Saturation Limit) throughout the entire process. Usually the transport air is injected at a significantly higher temperature (typically above 120° C.) and high transport gas flow rates are required. Such processes satisfy the requirements for aseptic packaging of food containers which can withstand such high temperatures. However many medical devices such as those employing fiber-optics, power tools, endoscopes etc are sensitive to heat and cannot be treated by vapour based processes subjected to such elevated temperatures, and therefore cannot be efficiently treated by hydrogen peroxide vapour at atmospheric pressure.

In 1979 Moore et al (U.S. Pat. No. 4,169,123) and Forstrom (U.S. Pat. No. 4,169,124) showed that hydrogen peroxide vapour could be an effective sterilant at below 80° C., given sufficient time. Spore strips were placed in a sealed package with a small amount of hydrogen peroxide solution and heated at above 60° C. for 24 hrs. By conducting the tests under vacuum, sterilization was reportedly achieved in 30 to 60 minutes, but sterilization could not be achieved in less than 6 hrs at atmospheric pressure at below 80° C.

To date, no gas or vapour systems using acceptable sterilants such as hydrogen peroxide have been sufficiently effective at atmospheric pressure and below 70° C. and to be commercialised for sterilization of medical instruments.
Gasses, Plasmas, and Vaporized Sterilizing Agents, at Reduced Pressure Vacuum systems greatly facilitate the vaporization of sterilants at below 70° C. However, processes which operate at reduced pressure suffer from the general disadvantage that vacuum pumps, pressure vessels, vacuum seals and such like are required in the design of the equipment used. This reduces reliability and adds greatly to capital and maintenance costs, to energy and other running costs, as well as to cycle time. Commercially available vapour and plasma systems have a capital cost ranging from about US$75,000 for a 50 liter unit to about US$180,000 for a 200 liter unit. In such systems the combined time required for pumping down to the required vacuum, sterilization, and for subsequent drying of endoscopes is greatly in excess of 20 minutes. More importantly, the reduced pressure is not compatible with longer flexible lumens because of the sealed airspace between the lumen and the outer sheath of the flexible endoscope, and only short flexible endoscopes up to 30 cm in length can be treated with vacuum systems.

Most vapour based processes are conducted under reduced pressure, and of these, many employ deep vacuum. Following the work of Moore and Forstrom, a great deal of research was directed at vapour processes at reduced pressure. Vapour based sterilization processes conducted at reduced pressure are described in for example U.S. Pat. Nos. 4,642,165; 4,943,414*; 4,909,999, 4,965,145 5,173,258, 5,445,792*; 5,492,672*; 5,527508*; 5,556,607*; 5580530*; 5,733,503*; 5,869,000*; 5,906,794; 5,508,009; 5,804,139; 5,980,825*; 6,010,662; 6,030,579*; 6,068,815*; 6,589,481* 6,132,680*; 6,319,480*, 6,656,426* Of these several (marked with an asterisk) claim to have success in sterilizing lumens or mated surfaces, and demonstrate the difficulty that these systems represent. In sub atmospheric pressure vapour processes the best results have been achieved by starting with a concentrated 50% peroxide solution (unless otherwise specified all peroxide concentrations referred to herein are percentage by weight), reducing the pressure so as to selectively vaporise water, and thus concentrate the remaining peroxide. Water is removed through the vacuum pump. The vapour process needs to start with a high concentration of peroxide, since otherwise the time taken to vaporise and pump out the water is too long. The processes can't start with more concentrated peroxide because higher concentrations would represent a danger during transport and handling. Even at 50% concentration, hydrogen peroxide requires special packaging to protect users.

The most successful of the sub atmospheric pressure, low temperature, sterilization processes involve forming plasmas from the vapour, eg hydrogen peroxide plasmas. Plasma systems avoid the use of high temperatures by operating at sub-atmospheric pressures. Typically these systems operate at below 0.3 torr. While plasma has the advantage that the peroxide solution used may be in concentrations of as low as 1-6% by weight, in commercial practice the starting solution of peroxide is greater than 50% to reduce cycle time. This involves special precautions in shipping, storage and handling, since peroxide concentrations of 50% and above are corrosive to skin or severe irritants, while 35% and below are considered safer to handle. The necessity for sub atmospheric pressures is an enormous disadvantage since it greatly lengthens treatment time which is costly, and requires the use of high vacuum seals, vacuum pumps, pressure vessels, special valves etc. The requirement for vacuum equipment greatly reduces reliability and increases capital outlay and maintenance complexity. The plasma process is completely ineffective when even traces of moisture are present—The STER-RAD™ plasma process is aborted if moisture is detected at ppm levels. The vast majority of medical instruments that are recommended for low temperature and chemical sterilization, for example endoscopes, face masks, respiratory hoses etc, are difficult to dry and especially so when they were prewashed before sterilisation. An advantage of vacuum systems over liquid systems is that if condensation of the sterilant on the surface can be avoided, the sterilant can be removed without the need for rinsing.

Although by far the most costly processes to install and to operate, high vacuum processes have to date been the most effective for treating mated surfaces and lumens when applicable. However, this system is not applicable for long flexible endoscopes and can only be used with lumens up to about 25-30 cm in length.

Aerosol Processes.

The present process is an improved aerosol process. While aerosols have been used to sterilize packaging materials, to date it has not been possible to use aerosol systems to treat endoscopes and the like, and aerosols have not been adopted for sterilizing medical instruments. Although an aerosol of ethyl alcohol was proposed for disinfecting breathing apparatus as early as 1965 (Rosdahl GB 128245), that method is not suitable for sterilizing medical instruments, among other reasons because it does not solve the problem of mated surfaces, and because ethyl alcohol is not sporicidal. That method has not been adopted commercially despite being known for forty years.

Known peroxide nebulants in the prior art are in the form of a mist generally having a mean particle size upwards of about 5 microns. These have been employed to treat substrates that were fully exposed. Hoshino (U.S. Pat. No. 4,296,068) described a process for sterilizing food containers in which a mist of sterilizing particles, formed by spray nozzles, and having a diameter of about 20-50 microns, are entrained in air heated to 50-80° C. Kodera (U.S. Pat. No. 4,366,125) combines a similar process using 10 micron droplets in combination with UV radiation for treating sheet material. Blidshun describes a peroxide aerosol having particles of 2-5 microns.

In 1998 Kritzler et al. (PCT/AU99/00505) described a process in which a nebulant consisting of from 1% to 6% peroxide in combination with a surfactant is recycled through a nebulizer and through a sterilization chamber without introduction of an external carrier gas. Although that process was capable of achieving log 6 reduction of B. subtilis within about 60 seconds on exposed open surfaces, and despite the initial promise, subsequent work reported here revealed that the process was unable to achieve 6 log reductions of Stearothermophillus (ATCC 7953 as used in STERRAD® CycleSure biological indicator) in less than 30 minutes on open surfaces. Moreover, the time taken to treat (sterilize, dry, and remove residuals) occluded surfaces, mated surfaces or lumens was unacceptably longer. Therefore this process was uncompetitive with vapour systems for sterilizing lumens and mated surfaces. Moreover the process left high (3 mg/cm$^3$) peroxide residuals on the surface, removal of which further added to processing time.

An advantage of hydrogen peroxide aerosol systems used to date is that the liquid nebulised had a concentration off 35% or less of hydrogen peroxide in the starting material which was considered safe to handle. However no aerosol sterilization systems developed to date have been satisfactory for sterilizing medical instruments and all have suffered from the following disadvantages:—

Firstly, aerosols have been unable to penetrate lumens and between mated surfaces of articles or into occluded areas of sterilization chamber in an acceptable time i.e. the time required for aerosols to achieve sterilization with lumens and mated surfaces was much longer than desired.

Secondly, the overall time required to achieve sterilization (i.e. a log 6 reduction in concentration of spores) at below 70° C. for some micro-organisms (for example resistant strains of Bacillus Stearothermophilus such as the ATCC 7953 strain), was much longer than desired.

Thirdly, when hydrogen peroxide is present in the form of small droplets (sprayed, ultrasonically nebulised, etc), the particles have a tendency to deposit as droplets on surfaces and the residual layer of peroxide is a potential problem. Medical instruments, food packaging and other disinfected items need to be stored dry to avoid re-contamination. Also surgical instruments must not contain residual peroxide at levels higher than 1 microgram/sq. cm. Eliminating residual peroxide is very difficult: It requires either washing which introduces the associated problems previously discussed in connection with liquid systems, prolonged periods of high temperature drying (which completely negate any advantages arising from fast kill times and low process temperature) or requires use of catalase or other chemical means to decompose peroxide (which still requires drying and which creates a series of problems with the residual chemicals left on instruments) or the use of vacuum.

In summary, it can be said that none of the sterilization methods currently available is entirely satisfactory for sterilizing medical instruments, and especially heat sensitive ones. More particularly, to date no process has been capable of (i) complete sterilisation of mated surfaces or lumens in under 20 minutes, (ii) at temperatures below 70° C., (iii) while yielding a dry ready-to-use product or surface (iv) without occupational health or environmental concerns. Moreover, the best commercially available processes suffer from major additional disadvantages. In the case of vapour and plasma systems pressure reduction is required, and commercial systems utilise hydrogen peroxide at concentrations of 50% or more as a starting material, requiring special packaging and handling. In the case of liquid systems a final rinse is required. Surveys of health professionals have repeatedly shown that the combination of achievement of criteria (i) to (iv) without either pressure reduction or rinsing would be highly desirable. Similar considerations apply to sterilization of other surfaces where pressure reduction and rinsing are often even less practicable.

Any discussion of the prior art throughout the specification should in no way be considered as an admission that such prior art is widely known or forms part of common general knowledge in the field.

OBJECT OF THE INVENTION

It is an object the present invention to provide a method of sterilization which avoids or ameliorates at least some of the disadvantages of the prior art.

It is an object of preferred embodiments to provide an improved method of disinfection or sterilization that can be conducted without reduction in pressure, without the need for rinsing, and without requiring an article undergoing treatment to be heated to above 60° C., and of highly preferred embodiments to achieve a log 6 reduction in micro-organism concentration on the surface of an article undergoing sterilization within 20 minutes. It is a further object of highly preferred embodiments of the invention to achieve such log 6 reduction within 20 minutes when the micro-organisms are situated between "mated surfaces", or in an endoscope lumen.

Another object of preferred embodiments of the invention is to disinfect or sterilize an article at atmospheric pressure and without leaving significant residual levels of hydrogen peroxide on the article's surface. In highly preferred embodiments, in which an endoscope or the like instrument is sterilized, it is an object to have the instrument dry and ready to use within 20 minutes.

It is a further object of the invention to provide an improved sterilizing agent.

While the invention is directed primarily towards sterilization, it will be understood that it also provides advantages when used for the less exacting goal of disinfection in comparison with other methods, for treatment of open and other surfaces, and for surfaces other than those of medical instruments Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to".

BRIEF STATEMENT OF INVENTION

According to a first aspect the present invention provides a method for disinfecting or sterilizing a surface comprising the steps of
(1) nebulising a solution comprising a sterilizing agent in a solvent to form a nebulant of finely divided particles of the solution in a gas stream, said solution including a solvent having a lower boiling point than the sterilizing agent;
(2) subjecting the nebulant to energy of a kind and for a duration sufficient to vaporize solvent in preference to sterilizing agent, whereby to increase the concentration of the agent in the nebulant particles;
(3) removing solvent vaporized in step 2 from the gas stream at or above atmospheric pressure and, if necessary, cooling the nebulant to below 70° C.; and
(4) exposing said surface to nebulant from step 3 for a time sufficient to sterilize the surface.

As herein used the term "nebulant" describes droplets of liquid (i.e. finely divided liquid particles) entrained in a gas stream. A system of liquid droplets entrained or suspended in a gas is an "aerosol".

In a highly preferred embodiment of the invention, all the steps are conducted at atmospheric pressure or above and the method is conducted using hydrogen peroxide as the sterilizing agent. In the first step a 35% solution of hydrogen peroxide solution in water is nebulised, for example, by means of an ultrasonic transducer driven nebulizer which entrains particles of solution ("micro-droplets") having an average diameter of greater than, for example 2 microns in a gas stream. The gas stream may initially be unfiltered, untreated air which is drawn from the sterilization chamber and subsequently recirculated by a fan or pump, the air becoming sterile in the process. In the second step the micro droplets in the aerosol issuing from the nebuliser are heated, for example, by passage over a heating element, which transfers sufficient energy to the solution particles to vaporize water from the droplets. The energy input is controlled to ensure that the energy acquired by the droplets is insufficient to raise the droplet temperature to the boiling point of the peroxide. Consequently water vapour is flashed off in preference to hydrogen peroxide. As a result the hydrogen peroxide concentration in the nebulant micro droplets increases to about 60% to 80% while the particles shrink to an average diameter of less than 1 micron (preferably less than 0.8 micron). We term the resulting finely divided particles in this aerosol "nano particles" or collectively a "nano-nebulant". In the third step, water vapour is removed from the gas stream at or above atmospheric pressure, for example by using a cold trap, a molecular sieve or desiccant, a semipermeable membrane device, or other water removal means operable at or above atmospheric pressure, while leaving the nano-particles (sub micron particles of concentrated peroxide solution) in suspension in the gas stream. The surface to be sterilized, for example of a medical instrument, is then exposed to this nano-nebulant in a sterilization chamber for a time sufficient to sterilize the surface. In preferred embodiments simple exposed surfaces have been sterilized within 3 minutes exposure time (total cycle time 5-10 minutes) and mated surfaces have been sterilized within 10 minutes exposure time, (total cycle time 15-20 minutes), in each case at atmospheric pressure. This allows an instrument to be recycled within 20 minutes including preconditioning and drying. If the solvent removal step does not involve cooling it may be desirable to cool the nano-nebulant prior to admission to the sterilization chamber.

It is preferred that the nano-nebulant from the chamber is recycled from the chamber to the nebulizer gas inlet and fresh nebulant may be added, but in other embodiments the nano-nebulant may simply be vented, or more preferably is passed through a catalytic or other process to remove the hydrogen peroxide prior to venting.

According to a second aspect the invention provides a process according to the first aspect wherein the surface is a mated surface or a lumen and wherein a 6 log reduction in micro-organism load in a mated surface sterilization test (as herein defined) or a lumen sterilization test (as herein defined) is achieved within 20 minutes.

According to a third aspect the invention consists in a novel nebulant comprising a solution of hydrogen peroxide suspended in finely divided form wherein the liquid particles have concentration of greater than 60 wt % of hydrogen peroxide, and an average diameter of less than 1.0 micron. Preferably the droplets have an average diameter of less than 0.8 microns. It will be appreciated that in prior art aerosol systems the peroxide liquid particles have had a concentration of less than 35% wt of hydrogen peroxide and an average diameter in excess of 2 microns. The relationship between particle size and fall velocity of particles in an aerosol is non linear, and so a small reduction in particle diameter greatly increases suspension stability as well as increasing the total surface area of the gas/liquid interface.

Desirably, the nebulant according to the third aspect has a peroxide density (grams of hydrogen peroxide/liter of aerosol) much greater than the peroxide density of a vapour at just below its saturation limit at a corresponding temperature and humidity.

Indicatively the maximum concentration of hydrogen peroxide vapour/per cubic meter (peroxide density) at varying temperatures and relative humidities ("RH") is shown in Table 1:

TABLE 1

Max. peroxide vapour concentration using initial 35% $H_2O_2$ solution (mg/liter)

| Temperature (° C.) | 10% RH | 20% RH | 40% RH | 80% RH |
|---|---|---|---|---|
| 20 | 0.97 | 0.85 | 0.62 | 0.14 |
| 40 | 4.13 | 2.59 | 2.66 | 0.63 |
| 60 | 14.4 | 12.60 | 9.1 | 2.31 |

The maximum concentration of 35% peroxide vapour at 40° C. and 40% RH is 2.66 mg/liter. The concentration/per cubic meter (density) of hydrogen peroxide aerosol of the invention at 40° C. is preferably greater than 20 mg/liter and more preferably greater than 45 mg/liter at a relative humidity ("RH") of for example above 40% and at atmospheric pressure.

For preference the aerosol gas phase is kept at a relative humidity of from 40%-60%. In highly preferred embodiments of the nebulant, the temperature and the humidity are selected within the area indicated as "reducing a bio-burden by log 6" in less than 20 minutes in FIG. 10, eg. at above 40%-60% at 40° C. for at least 14 minutes. It will be appreciated that in the prior art aerosol processes the gas stream has generally had a RH of 90-100%, while in vapour processes the RH is as close to 0% as possible and generally below 20%

According to a fourth aspect, the invention provides an apparatus comprising in combination:
(1) means adapted to produce a nebulant comprising finely divided particles of a solution suspended in a gas, the solution comprising a solute and a solvent;
(2) means for supplying sufficient energy to the nebulant to selectively flash off at least some of the solvent as a vapour, whereby the concentration of solute in nebulant particles is increased; and
(3) means to separate solvent vapour from the nebulant after step 3 at atmospheric pressure, and if necessary then cooling the nebulant to below 70° C.
(4) means for exposing a surface to be sterilized to the nebulant from step 4.

In preferred embodiments of the apparatus, means are provided for controlling the energy supplied in step (2) to ensure that solvent is vaporised in preference to solute and that relatively little of the solute is vaporized.

In preferred embodiments of the method of the invention, the surface to be sterilized is the surface of a medical or dental instrument, or other appliance or article, and may include an occluded surface, a lumen or a mated surface. Such articles may be placed in a sterilization chamber which is provided with one or more access ports which may be sealed from the surrounding atmosphere, or may be sterilized within a disposable chamber or reusable cassette which may also optionally serve as a storage container for the sterilized article until its next use.

The method of the invention can be conducted under static or dynamic conditions.

The invention will now be more particularly described by way of example only with reference to specific embodiments.

BRIEF DESCRIPTION OF THE DRAWINGS

FIG. 11 is a graph showing a relationship between biocidal efficacy, peroxide delivery rate, and aerosol flow velocity.

FIG. 12 is a graph showing a relationship between biocidal efficacy and peroxide delivery rate, and nebuliser power supply.

FIG. 16 presents Table 1, which indicates the maximum concentration of hydrogen peroxide vapour/per cubic meter (peroxide density) at varying temperatures and relative humidities ("RH").

FIG. 17 presents Table 2, which shows the relative humidity in the sterilization chamber of FIG. 1 over a 15 minute cycle in accordance with Example 1.

FIG. 18 presents Table 3, which shows the microbiological efficacy results of the treatments performed in Example 3.

FIG. 19 presents Table 4, which provides the operating parameters of the sterilization apparatus and the microbiological efficacy results of the treatments performed in Example 4.

FIG. 20 presents Table 5, which shows the microbiological efficacy results of the treatments performed in Example 5.

FIG. 21 presents Table 6, which shows the microbiological efficacy results of the treatments performed in Example 6.

FIG. 22 presents Table 7, which shows the microbiological efficacy results of the treatments performed in Example 7.

FIG. 23 presents Table 8, which provides the weight of peroxide on an open surface and microbiological efficacy results after the treatments performed in Example 8.

FIG. 24 presents Table 9, which provides a comparison of nano nebulant efficacy with vapour efficacy according to Example 9.

FIG. 25 presents Table 10, which provides the relationship of $H_2O_2$ delivery rate to air flow velocity, nebulizer power supply, nebulizer duty cycle and % of initial $H_2O_2$ solution to log reduction in bio-burden for mated surfaces under various conditions of operation of apparatus according to FIG. 2.

FIG. 26 presents Table 11, which shows the effect of duty cycle on sterilization efficacy and residuals using a cassette similar to that in FIG. 8A containing a probe to be sterilized according to Example 10.

In each of the embodiments described with reference to FIGS. 2-8, parts corresponding in function to parts shown in FIG. 2 are identified with the same numerals.

DESCRIPTION OF PREFERRED EMBODIMENTS

A first preferred embodiment of the invention will be described in which a solution consisting of 35% of hydrogen peroxide in water as the solvent, is nebulised in step (1) for use in the invention.

Figure 2:
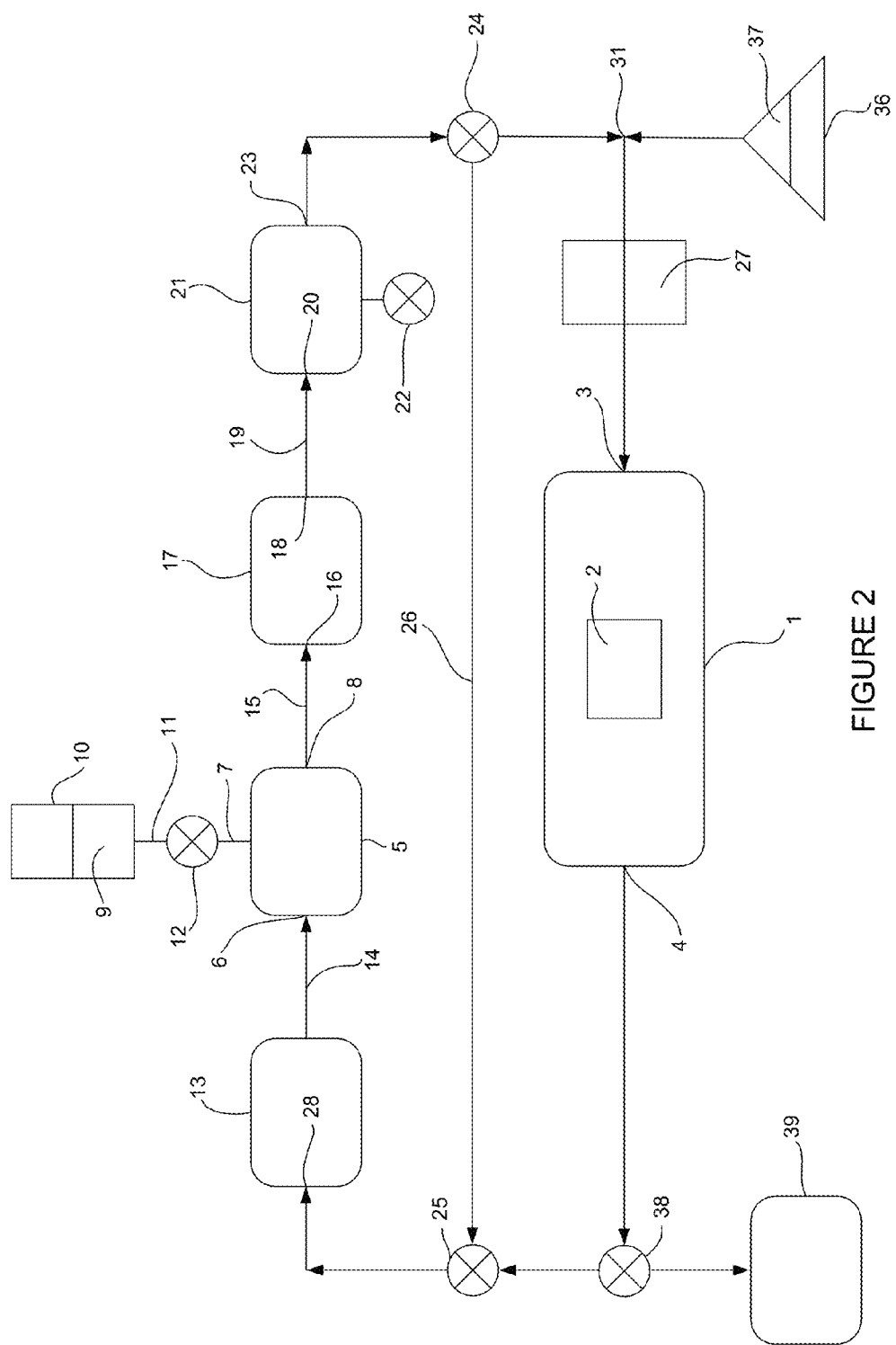
FIG. 2 is a schematic diagram of a first embodiment of apparatus according to the invention

With reference to FIG. 2 there is shown apparatus comprising a chamber 1 which is sealed from the atmosphere and is provided with one or more sealable doors, ports or other openings (not illustrated in FIG. 2) by means of which an article to be sterilized 2 can be placed into chamber 1. Chamber 1 is provided with a gas stream inlet port 3 and exit port 4. Desirably chamber 1 is thermostatically controlled, at for example 45° C., by means of a jacket or the like (not illustrated), and/or is thermally insulated.

Chamber 1 can be selectively connected with a nebuliser circuit, a drying circuit, or a catalytic destruction circuit as hereinafter described.

In the embodiment of FIG. 2 a "nebuliser circuit" includes a nebuliser 5 having a gas stream inlet 6, a liquid inlet 7 and a nebulant outlet 8. In the present embodiment nebuliser 5 is an ultrasonic nebuliser incorporating an ultrasonic transducer having a resonant frequency of 2.4 MHz driven by conventional control circuitry (not illustrated) and is more particularly described hereinafter with ref to FIGS. 3, 4. However other means for nebulisation may be employed.

Nebuliser 5 is adapted to receive a liquid sterilant solution 9 (in this example 35% hydrogen peroxide in water) from a reservoir 10 via a feed line 11 including a valve 12 communicating with nebuliser liquid inlet 7. A gas stream is driven via fan 13 and line 14 to gas stream inlet 6 of nebuliser 5 under a small but positive pressure. In the present example sterilant 9 fed to nebuliser 5 via line 11 is a 35% solution of hydrogen peroxide in water and the gas stream admitted to inlet 6 via fan 13 and line 14 is air. In operation nebuliser 5 generates an aerosol of finely divided particles (droplets) of 35% hydrogen peroxide solution suspended as a mist in the air stream. The average diameter of droplets of the aerosol (nebulant) at the nebulizer outlet is desirably in the range of 2-10 microns.

The aerosol from nebuliser outlet 8 is fan driven via line 15 to the inlet 16 of a heater or heat exchanger 17 having an outlet 18. In the present embodiment, heater 18 consists of one or more ceramic electrical resistance heating elements (not illustrated) whose energy output is adjusted in response to signals from various sensors for example temperature sensors, flow rate sensors, thermal conductivity sensors, humidity sensors or the like, as will be hereinafter discussed. As the nebulant flows through heater 17 conditions (flow rate, contact time, temperature) are controlled so that water evaporates from the aerosol particles, and the peroxide in the droplets becomes concentrated. Also the average particle size decreases to below 1 micron and preferably to below 0.8 microns, that is to say, the micro droplets in the gas stream become nano-nebulant droplets. The concentration of peroxide in the micro nebulant may become 70-80% or more.

The gas stream emanating from heater 17 at outlet 18 containing smaller droplets of more concentrated peroxide liquid, and also containing water vapour driven from the droplets, is directed from heater outlet 18 via line 19 to the inlet 20 of solvent removal device 21. In the present example the water removal device 21 is a cold trap in which water vapour is condensed and is removed at drain 22 for liquid analysis or disposal. The cold trap may, for example, utilize a Peltier device to achieve cooling. The nebulant issues from the cold trap from outlet 23 at a temperature of below 70° C., and preferably at below about 55° C. However, other means 21 for water vapour removal at atmospheric pressure may be substituted for the cold trap as hereinafter discussed.

The gas stream now containing the nano-nebulant and a reduced water vapour concentration exits water removal device 21 at outlet 23 and is initially directed via valves 24, 25 and bypass line 26 to the suction side 28 of fan 13 to be recirculated through nebuliser 5, heater 17 and water removal device 21 until the gas stream reaches a desired hydrogen peroxide concentration, particle density, and level of moisture reduction. These levels are discussed hereinafter.

Once the desired gas stream concentration has been achieved in the nebulizing circuit, the sterilizing chamber is brought on line with the nebulising circuit. That is to say valves 24 is reset so as to divert the flow exiting the moisture removal device 21 from outlet 23 to gas inlet 3 of sterilization chamber 1 and valve 25 is then or simultaneously reset so that sterilization chamber gas outlet 4 is placed in communication with the suction side 4 of fan 13. Bypass line 26 is thereby isolated. Chamber 1 is now in "on-line" mode.

Assuming an article 2 to be sterilized was previously placed in chamber 1 and the chamber sealed from the atmosphere the chamber will now be flushed with nebulant being recirculated by fan 3 via the nebuliser 5 heater 17 and water removal means 21. It is important to note that if the article being sterilized is temperature sensitive, and if the nebulant exiting water removal device 21 is at a temperature of above about 55° C. (which may be the case if a cold trap is not used for water removal), and certainly if it is above 70° C., means 27 for cooling the nebulant prior to entry to sterilization chamber 1 may be required.

The nebulant may be recirculated through sterilization chamber 1 in "on-line mode" as described above for a period sufficient to achieve sterilization, or after a short time sufficient to build up a desired concentration in the chamber, the chamber containing the nebulant may be isolated for a period, by redirecting valves 24, 25 to re-establish the nebuliser circuit in by-pass mode, leaving the chamber sealed with a predetermined volume and concentration of nano-nebulant in "isolated mode" for a period, or the chamber may be switched repetitively between on-line mode and isolated modes for predetermined periods.

After a contact time sufficient to achieve a desired level of disinfection or sterilization, chamber 1 may put into drying mode. This may be achieved using a separate drying circuit involving drawing in air via a hepa filter 36, heating it by means of heater 37, and directing it over the disinfected surface to remove any residual moisture condensation of peroxide condensation from the surface. Alternatively, drying can be achieved utilizing elements of the nebulizer circuit by circulating dry warm air through the heater 17, water removal unit 21, and chamber 1, but bypassing (or not energizing) the nebulizer 5. After a satisfactory level of dryness is achieved, the chamber is placed on line with the biocide disposal circuit. For example, hepafiltered air under a positive pressure may be admitted via inlet 36, directed into chamber 1 via non return valve 31 at chamber gas inlet port 3 and used to flush peroxide from chamber 1, the flushing—air emitted from gas outlet port 4 being directed via a valve 38 to a catalytic destruction unit 39 where for example peroxide is converted into water and oxygen and thus any residual hydrogen peroxide is rendered suitable for harmless disposal in the environment. The catalytic destruction circuit may involve recirculation through the catalytic converter till destruction is complete. Catalytic destruction of hydrogen peroxide is well known and any suitable method or apparatus can be employed.

It will be understood that in use the system is a dynamic one. As the gas stream is recirculated, nano-nebulant enters the nebulizer and entrains freshly sonicated micro-droplets so that the stream exiting the nebulizer will comprise nano particles from previous passes as well as micro droplets, but the average particle size will progressively decrease. The amount of water vapour to be removed will also become progressively less.

The invention will now be further described by way of example only with reference to specific examples.

DESCRIPTION OF PREFERRED EMBODIMENTS OF THE INVENTION

Figure 3:
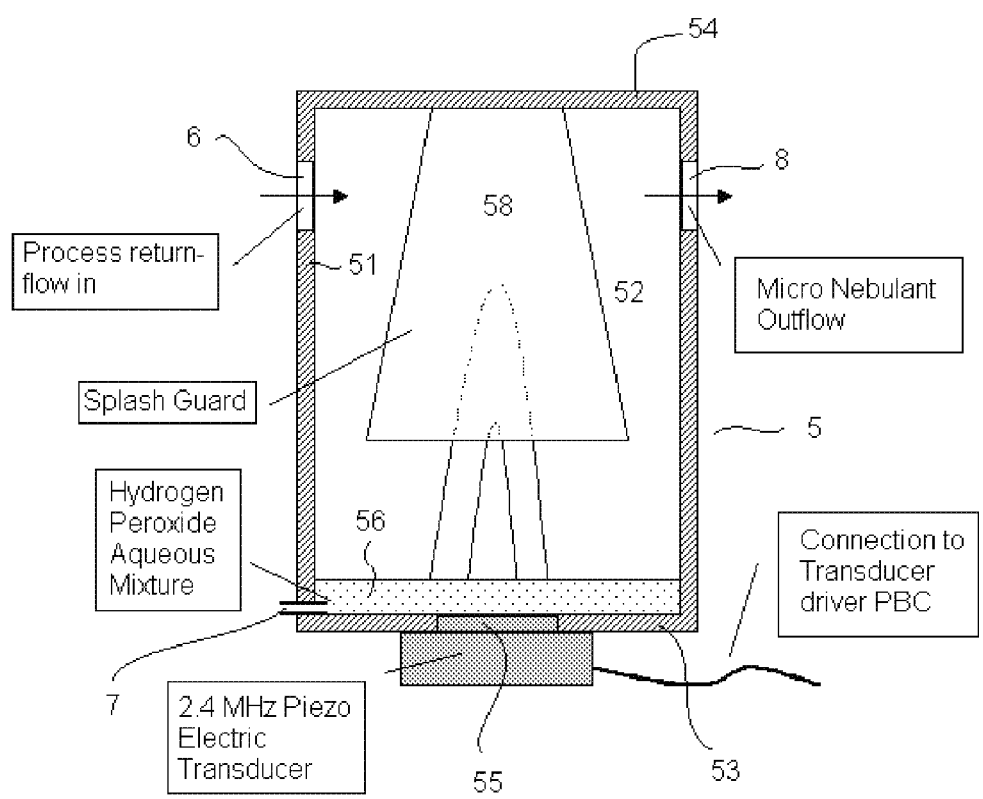
FIG. 3 is a schematic diagram showing nebuliser 5 of FIG. 2 in more detail.

A first embodiment of a nebulizer for use in the apparatus of FIG. 2 will now be described schematically with reference to FIG. 3, wherein parts having a function corresponding to parts in FIG. 2 are identified by the same numerals. FIG. 3 shows a nebulizer indicated generally at 5 and comprising a chamber defined by nebulizer walls 51, 52, floor 53, and ceiling 54. A gas inlet 6 pierces wall 51, while a nebulant outlet 8 pierces wall 52. Both the gas inlet and nebulant outlet orifices are situated near the upper end of the chamber and may in practice be fitted with connection spigots or threaded bosses (not shown) to facilitate connection to the circuit. A piezoelectric transducer 55 is removably mounted by suitable means to floor 53. A preferred transducer is a commercially available from APC International Ltd which is a 2.4 MHz crystal/stainless steel faced transducer providing a fluid atomisation rate of aprox. 350 cc/hr and operable at 48VAC, 0.6 amps, 29 watt and having an expected life of about 10,000 hrs use. Ultrasonic transducer 55 is driven by a suitable driver circuit and energized by a suitable power supply. In some embodiments of the invention a detector is used to monitor the transducer ultrasound output and provides a signal which can be used as a feedback control signal to control the operation of the ultrasonic transducer. These electronic circuits are conventional in the art. A frustroconical baffle 58 is mounted from ceiling 54 above the ultrasonic transducer and serves to direct any larger droplets falling back into the liquid to do so radially outwardly from the transducer while preventing larger droplets from being entrained in the air gas stream entering at 6 and exiting at 8. Hydrogen peroxide solution to be nebulized is shown as 56 and may for example be injected in a predetermined dose via a liquid feed port 7.

Figure 4:
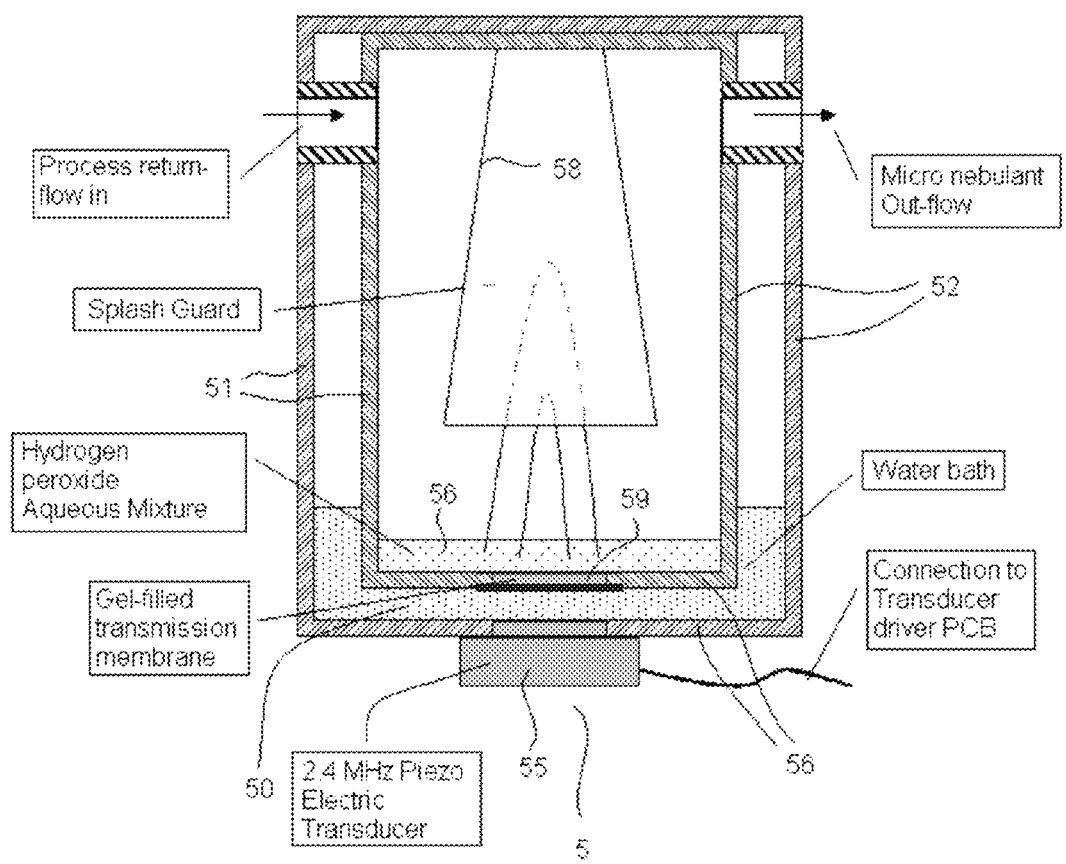
FIG. 4 is a schematic diagram of an embodiment of nebuliser 5 which differs from that of FIG. 3.

FIG. 4 shows a second embodiment of a nebulizer wherein parts having a function corresponding to parts in FIG. 3 are identified by the same numerals. The nebulizer of FIG. 4 differs from that in FIG. 3 in that it is provided with double walled inner walls 51, 52, and double walled floor 56, the double walls being spaced apart. In this embodiment a water bath or other ultrasound transmission fluid 60 is maintained between ultrasound transducer 55 and a membrane 59 mounted to inner floor 58.

Figure 5:
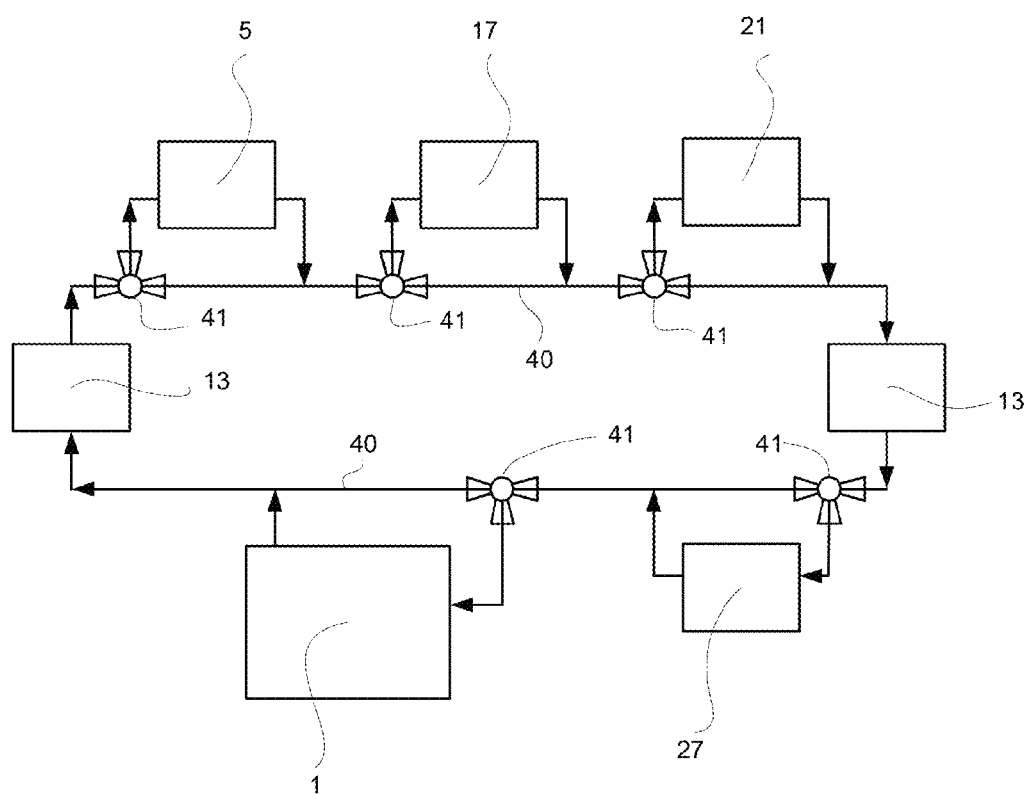
FIG. 5 is a schematic diagram of a second embodiment of apparatus according to the invention

A second embodiment of apparatus for conducting the method of the invention is shown in FIG. 5 wherein parts corresponding in function to parts shown in FIG. 2 are identified with the same numerals. The circuit of FIG. 5 is similar to that of FIG. 2, but units are independently connectable in series with the circuit and/or with other units.

Thus, in the embodiment of FIG. 5, one or more fans 13 drive a recirculating gas stream in a manifold 40. Each of Nebulizer 5, solvent vapourising heater 17, solvent vapour removal unit 21, sterilizing chamber 1, and optionally a cooler 27, can be connected in line (that is to say in series) with manifold 40, or can be isolated off line by valves indicated generically by numeral 41. It is thus possible to connect nebulizer 5, heater 7, solvent removal unit 21 and chamber 1 in series in which case the arrangement is similar to that of FIG. 2, or it is possible to have nebuliser 5 and vapour remover 21 isolated and to circulate a gas stream through the heater 17 and chamber 1 for drying purposes, and/or through heater 17 and vapour removal unit 21 for drying purposes and so on.

Figure 6:
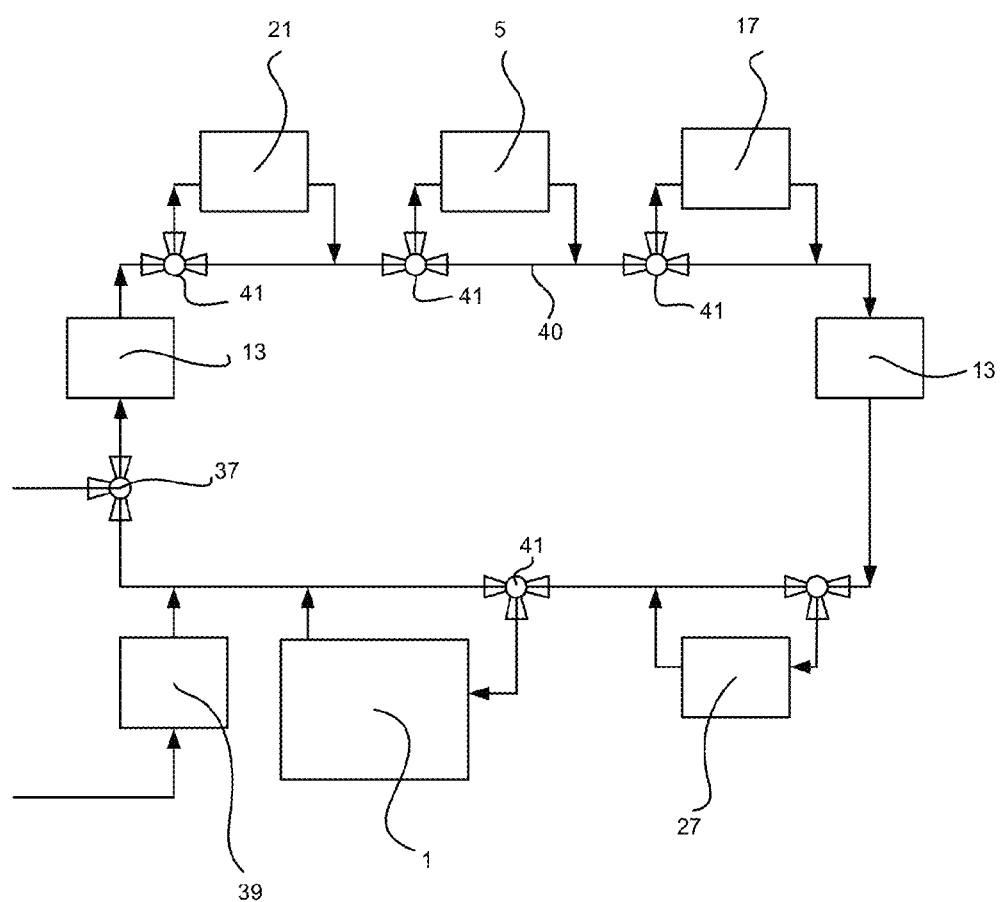
FIG. 6 is a schematic diagram of a variation of a third embodiment of apparatus according to the invention, being a variation of the second embodiment.

It will be understood that since the apparatus involves use of a recirculating gas or aerosol stream the order of the units may also be arranged in other sequences. For example, as shown for example in FIG. 6, wherein units performing the same function are identified with the same numerals as FIG. 5, the solvent removal unit 21 is disposed upstream of nebuliser 5, but since the aerosol can be recirculated with the sterilization chamber off stream until a desired nano-particle solution concentration, temperature, aerosol peroxide concentration and water vapour reduction have been achieved, the same results can be achieved as with the arrangement of FIG. 2. It will also be understood that in conducting the method the steps need not be performed sequentially and at least steps (1), (2), and (3) may be performed substantially simultaneously, or in a different sequence, although solvent removal cannot occur more quickly than solvent vaporisation occurs, and although step 4 cannot commence until sufficient solvent vapour has been removed.

It will be understood that the apparatus of FIGS. 2-6 may be provided with sensors for temperature, pressure, circulation speed, relative humidity, peroxide vapour concentration, peroxide liquid concentration and such like parameters and these may include automatic feedback and control circuits It will be understood that the apparatus can be varied in many ways without departing from the invention herein disclosed.

In the embodiments described above the sterilizing agent was a solution of hydrogen peroxide and was a 35 wt % solution in water which acted as the solvent. The preferred solvent for use with peroxide is water. Water boils at 100° C. while hydrogen peroxide boils at above 151° C. at atmospheric pressure. The solvent could for example be an aqueous or non aqueous alcohol chosen in combination with the sterilizing agent to be used. The addition to water of ethyl alcohol results in an azeotropic mixture which lowers the boiling point of the solvent and this enables the water to be "flashed" off at lower temperatures than would otherwise be possible. The addition of other azeotropic agents would be equally beneficial. The use of azeotropes to facilitate the removal of solvent from the nebulant solution particles is within the scope of the invention. It is envisaged that for some biocides non aqueous solvents or a combination of suitable solvents could be employed.

In the case of hydrogen peroxide, as the water flashes off, the concentration of the sterilizing agent increases. If a 35% peroxide solution is used in the invention the micro nebulant after the heating and water vapour removal steps will have a concentration of for example 60 to 80%. This has the advantage that the starting material can be handled relatively safely, that concentration occurs during the process and that thereafter there is no further need to handle the peroxide. Also, the average particle size is greatly reduced, the micro nebulant particles in preferred embodiments having a mean diameter of less than 1 micron, more preferably less than 0.1 micron. The small particle size results in a very stable suspension with negligible settling out, provides a significant increase in the liquid/gas interfacial area, and in very high concentrations of liquid sterilant per liter of nebulant. The inventors believe that there may be a higher concentration of peroxide molecules at the gas/liquid interface in these nano particles than occurs in micro particles. Solutions of a lower or greater concentration than 35% can be used as a starting material and excellent results have been obtained with hydrogen peroxide solutions of 1% or 3% as well as with solutions of 40%, but the time taken to achieve a satisfactory result with mated or occluded surfaces was less than optimum with peroxide concentrations below 30%, and handling issues result in a preference for concentrations of below 35%. While preferred embodiments described have employed aqueous solutions of hydrogen peroxide as the sterilizing agent, solutions of other peroxides and peroxy compounds can be employed as well as solutions of peroxy complexes (including non water soluble complexes in organic solvents). Sterilizing agents other than peroxides may also be used in the invention, including without limitation halo compounds, phenolic compounds, halogen phenolic compounds and other known biocides, with appropriate choice of solvent.

The particles or droplets of sterilant solution (35% hydrogen peroxide in aqueous solution in the preferred embodiment) which are formed from the solution by the nebuliser are entrained in a gas stream which in the preferred embodiment is air. It is a significant advantage of preferred embodiments of the invention over prior art that they do not require a source of filtered sterile air. Instead the invention is able to draw non sterile air from the sterilization chamber, and sterilize it while recirculating it in use. However, if preferred, aseptic filtered air could be employed. The gas stream is not necessarily air, and could for example be an inert gas such as nitrogen, or argon; or could be oxygen or ozone.

Although the invention has been described with reference to nebulization by means of an ultrasonic nebulizer, it will be understood that other means for nebulization including sprays, jet nebulizers, piezoelectric nebulizers, and such like nebulant generating devices may be employed. Desirably, the suspended droplets issuing from the nebuliser have an average diameter of less than 10 microns and more preferably less than 5 microns. As described in our co-pending application (PCT/AU99/00505), smaller particles can be obtained by including a surfactant for example an alcohol, in the sterilant solution when using ultrasonic nebulization. It is not necessary for an ultrasonic nebuliser to be run continuously and in preferred embodiments of the invention the nebuliser is switched on and off cyclically, (or at irregular intervals) being run for example about 20 seconds per minute.

The nebuliser may be fed with sterilant solution on a continuous or intermittent basis from a bulk supply, e.g. while maintaining a predetermined liquid level in the nebuliser, or may be provided with a single shot dosing system for example a cartridge providing sufficient solution for one or a plurality of sterilization cycles. Alternatively, a sterilant solution may be provided pre-packed in a capsule which may be placed in an adapted nebulizer so that the capsule is in contact with the ultrasonic transducer of the nebuliser. In this case means are provided for piercing the capsule so that it is able to release the solution as a nebulant. In another embodiment the sterile solution may be provided in a capsule having an integral ultrasonic transducer adapted to be energised via contacts extending through the capsule wall when the capsule is inserted in the nebuliser.

After formation of the aerosol, but prior to its admission to the sterilization chamber, the aerosol is subjected to an input of energy of a kind and for a duration sufficient to vaporize at least some of the solvent from the aerosol particles. In the embodiment described with reference to FIG. 2, this is achieved by passing the aerosol over one or more heating elements, which may be any conventional heating element, including but not limited to ceramic elements or the like. In such cases the temperature and heat exchange characteristics of the heating element are selected together with the gas flow-rate, temperature and humidity of the aerosol stream, so as to flash off the solvent, in the example water, as a vapour and substantially without vaporizing any significant amount of the peroxide. This is accomplished partly by selecting conditions so that thermal transfer to the solution particles in the aerosol raises the solution temperature to a point below the boiling point of the sterilization agent but above that of the solvent, but it is believed to be facilitated by the very great surface area of solution which is exposed to the carrier gas by the liquid in its finely divided particulate state and the relative ease with which water molecules are released from the liquid/gas particle interface.

Although in the preferred embodiment water is flashed off from the nebulized particles, by means of passage over a ceramic heating element, any conventional heating element may be used, or the energy required to achieve this could be transferred to the particles by other means including, without limitation, radiation for example infra red or laser radiation of suitable frequencies, microwave, RF or other radiation; induction; contact with heat exchangers; and other forms of heating including conduction, convection, or mechanical energy transfer means.

Although the mist particles may be instantaneously exposed to temperatures above 60 C.° for extremely short periods, for example during flow past any form of heating element at 700° C.-1000° C.—the flow rate is such that the bulk of the aerosol as a whole is either maintained at below 60 C.° and preferably below 45 C.° (or is subsequently cooled to such temperature by means of a cooling device or heat exchanger prior to being brought into contact with the surface to be sterilized). When heated, the droplets of nebulant which are visible to the naked eye as a mist or cloud become invisible to the naked eye although particle light scattering can be seen when a light beam is shone through the fine mist. However, as the temperature in the chamber is well below the boiling point of hydrogen peroxide at atmospheric pressure, the bulk of hydrogen peroxide is clearly not in a vapour phase. As the invisible sub micron droplets of sterilizing agent are not a vapour, they have herein been referred to as a "nano-particles". There is inevitably a small quantity of peroxide vapour in equilibrium with the liquid in the particles but no more so than with prior art nebulant systems, After vaporizing solvent in preference to sterilizing agent, the solvent vapour is carried in the gas stream along with the now smaller aerosol particles. The solvent vapour is then removed from the "nano-nebulant" at atmospheric pressure. In the embodiment of FIG. 2 that is accomplished by passing the carrier gas with the nano-nebulant and solvent vapour through a cold trap whereby the solvent vapour is condensed and removed from the gas stream. In the example in which the solution being nebulized is hydrogen peroxide in water, and water vapour is flashed off in step 2, the water vapour is condensed in step 3 leaving the gas stream containing a sub micron suspension of micro nebulant particles of 60-80% hydrogen peroxide. This step of vapour removal can also be carried out by other means including, without limitation, by passing the gas through a drying agent, desiccant, or through suitable molecular sieves, membranes, by passage through a centrifuge for example an adapted centrifugal fan, or by means of a suitable cyclonic separator, or the like. However if a cold trap is not used as the vapour separator, it may be necessary to cool the air stream prior to exposing the article to be sterilized to the air stream to ensure that the nano-nebulant is below a temperature at which an article in the sterilization chamber might be damaged.

Figure 7:
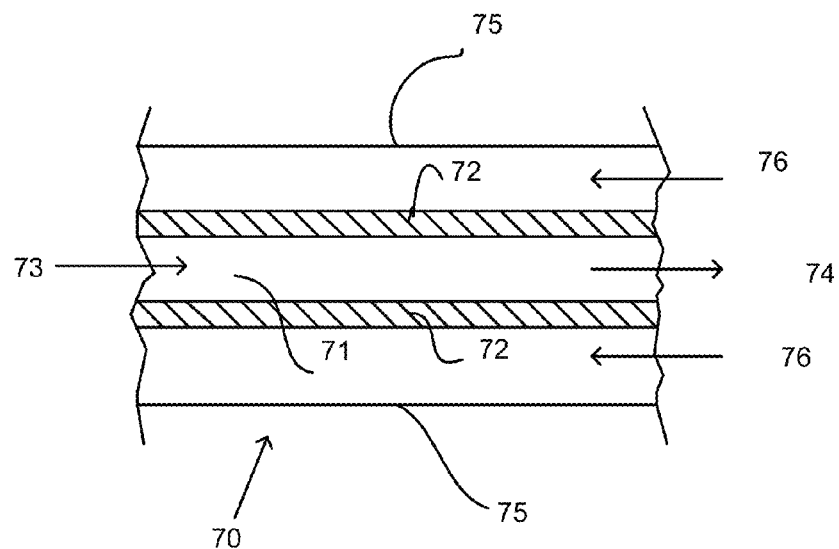
FIG. 7 is a schematic diagram of an embodiment of a novel solvent removal unit for use in the invention.

Another preferred method of solvent separation is shown in FIG. 7. In FIG. 7 there is shown in cross-section an apparatus 70 comprising a first tube 71 comprising a tube wall 72. The tube wall 72 is in whole or part constructed from a material which is porous to the solvent vapour but not to the nano-particles, for example KIMGUARD™. An aerosol containing nano-particles and solvent vapour flows through tube 71 in a first direction for example from inlet 73 to outlet 74.

Desirably, a counter current airflow 76 is established in a concentric tube 75 which assists in removal of solvent vapour diffusing through wall 72.

In the present use, which is novel, KIMGUARD™ fabric is used to separate water vapour from the peroxide mist droplets at atmospheric pressure, and can be used instead of the cold trap of FIGS. 2-6 or can be used in conjunction with a cooling or other water vapour removal means. KIMGUARD™ is a multilayer non woven polypropylene fibre fabric intended for use as a terminal sterile barrier for wrapped items such as surgical devices. It is impenetrable to micro-organisms. Other similar hydrocarbon fabrics for example TYVEK™ and SPUNGUARD™ in suitable grades may be substituted for KIMGUARD™. Wall 72 need not be a woven fabric and may be any other suitable semipermeable membrane which facilitates the removal of water while being impermeable by micro-organisms and nebulant particles.

Desirably at least one fan, or pump, is used to circulate the gas stream from the nebulizer, past the heating element, the water removal unit, and into and out of the sterilization chamber.

The sterilization chamber may be a simple chamber, may be jacketed or temperature controlled, and may be provided with supports for articles to be sterilized or special couplings, for example to connect an endoscope or otherwise direct flow of the nano-nebulant through one or more lumens.

The sterilization chamber may be in any suitable form for example may be a pouch, a cassette, a container, a chamber, a room, or the like.

Figure 8:
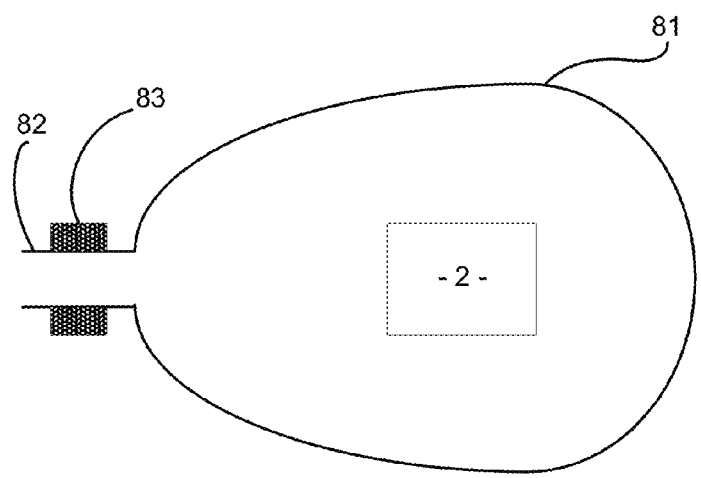
FIGS. 8 and 8A are schematic diagrams showing novel packages for use in the invention in vertical cross-section.

In highly preferred embodiments an article to be sterilized may be contained in a disposable pouch or cassette into which the nano-nebulant can be directed for example through a sealable port but which is porous to vapour allowing the article to be dried in the package and subsequently stored in the package in a sterile condition. A material suitable for this is KIMGUARD™, TYVEC™, or SPUNGUARD™ but other woven or non woven semipermeable membranes may be suitable. FIG. 8 illustrates an example of a package suitable for this use comprising a pouch having a flexible wall 81 made from KIMGUARD™ and having an inlet port 82 sealable at 83 by heat seal or induction heating or any other suitable means. Alternatively the inlet port may be provided with a non return valve. In other embodiments the package may be provided with both an inlet and an outlet port to facilitate connection to a circuit such as illustrated in FIGS. 2-5 in place of the sterilization chamber.

Figure 8A:
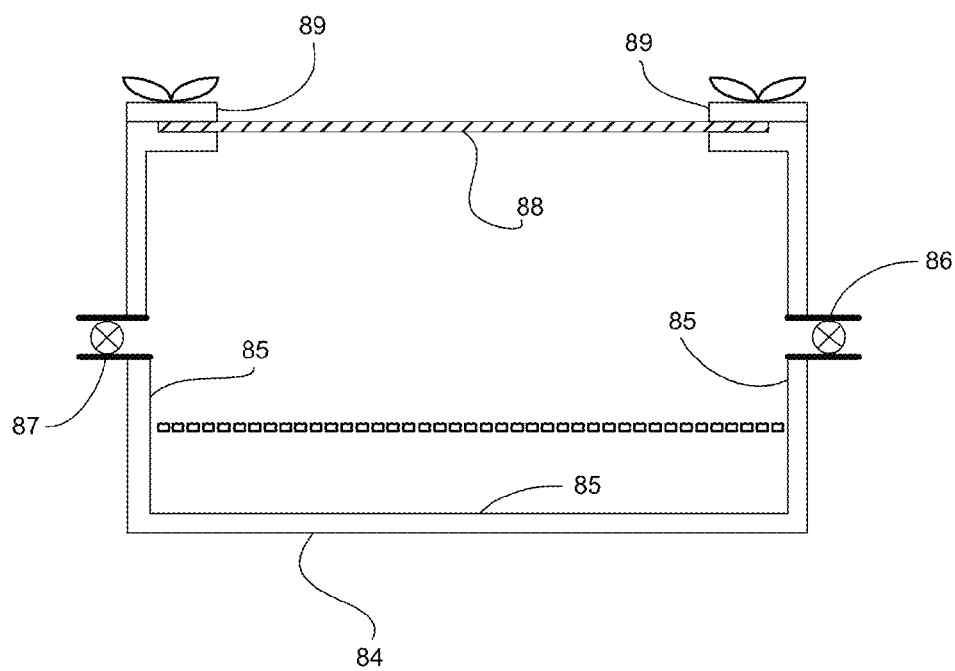

In highly preferred embodiments, the article to be sterilized (for example an ultrasound probe or endoscope) is contained within a sealable reusable cassette which has one or more openings covered with a fabric such as KIMGUARD™. The cassette may be placed within a sterilization chamber (such as chamber 1 of FIG. 2, 5 or 6). On removal of the cassette from the chamber, the article remains sealed inside the cassette within the sterile environment until the article is removed for use. A cassette is exemplified schematically in FIG. 8A wherein there is shown in cross-section a rectangular chamber 84 having impermeable walls 85, valved entry and exit ports 86, 87. A sheet of KIMGUARD™ 88 is stretched over an opening on one side of chamber 84, and held in place by a removable frame 89 whereby sheet 88 is clamped in place and in sealed attachment to the edges of the opening. If desired the sheet of KIMGUARD™ 88 mat be supported by a perforated plate or the like (not shown in the drawing) and a screen or grid 90 may be provided for supporting instruments above the cassette floor. It will be appreciated that in the prior art, containers employing TYVEK™ and the like have been used by (1) sealing an article therein, (2) admitting sterilizing gas or vapour from the exterior through the membrane to the interior, and then (3) using the membrane to protect the content from ingress of micro-organisms into the package until opened. In this invention: (1) the article is placed in the container, (2) the nano nebulant is admitted to the container, (3) water and/or peroxide vapour is allowed to exit from the container interior through the membrane to the container exterior at atmospheric pressure, and thereafter micro-organisms are prevented from ingress. In other embodiments the cassette may be substituted for the sterilization chamber. Or the cassette may be adapted to act both as a water removal stage and as a sterilizing chamber/storage container by combining features of the device described with reference to FIG. 7 with that of FIG. 8.

The surface to be treated is exposed to the nano-nebulant particles from step 3 for a time sufficient to sterilize the surface. Surprisingly, it has been found that the resulting nano-nebulant is not only more rapidly effective than prior art aerosols, but also is highly effective at penetrating mated surfaces, and treating occluded surfaces which are not directly exposed. While it is not clear why this is so, it may be that a very high density of nano-nebulant (for example 2.0 mg/l or greater at 40% RH) is distributed throughout the volume of the sterilization chamber while at the same time there is little or no actual condensation on the surface. The nano nebulant particles have a far greater surface area at the gas/liquids interface than the original micro nebulant particles and are significantly smaller in diameter, and consequently remain suspended for much longer periods. Without wishing to be bound by theory, the present applicants believe that the nano-particles impinge on the surface at a greater frequency than the prior art micro particles, and have a longer residence time on the surface than vapour molecules. In comparison with prior art aerosol processes, surfaces treated by the invention may be rapidly dried and are relatively uncontaminated by residual peroxide. When treating a lumen, it is preferred that the lumen be connected to receive a flow of the nebulant through the lumen. Desirably, the external and mated surfaces are also exposed to the nebulant in the chamber or cassette.

EXAMPLES

Unless otherwise specified the test methods set out below were used in the examples which follow:
Microbiology:

The species tested was *Bacillus stearothermophilus* (ATCC 7953) which has been indicated to be the most resistant to the peroxide and heat based disinfection processes. *Bacillus Stearothermophilus* spores were grown according to the "Schmidt method" using Nutrient Agar Plus 5 ppm $MnSO_4$ as described in Pflug (1999). Growth conditions ensured that the spore count relative to the vegetative form was almost 100%.
Potency Testing on Mated Surface and Other Carriers:

Sterile open carriers used were porcelain penicylinders as per the AOAC sporicidal method 966.04, as well as flat surfaces of varying composition. To simulate the mated surface assemblies presented on a flexible endoscope, the carriers used were sterile stainless steel washers of varying dimensions that were placed one overlying the other with the flat surfaces directly in apposition. Unless otherwise specified the washers were selected so that the mated surface area was 85 $mm^2$.

Penicylinders were inoculated as per the AOAC sporicidal method 966.04. In order to simulate soil, 5% horse serum and 340 ppm AOAC hard water was incorporated in the inoculum. The washers and other surfaces were inoculated with 0.01 ml of test suspension and then vacuum dried for 24 hours in a desiccator. Each carrier was inoculated to provide a contamination level of $1-5 \times 10^6$ cfu per carrier. For the mated surfaces testing another washer was placed directly over the inoculated, dried washer. When inoculated, the inoculum is sandwiched between the lower surface of the upper washer and upper surface of the lower washer, Recovery of Spore Survivors:

On completion of the disinfection cycle the carriers were aseptically transferred into 10 ml tubes of tryptone soya broth (TSB, Oxoid CM 131, Bassingstoke, United Kingdom) containing 100 microliters sterile catalase (Fermcolase 1000, Genencor International, Belgium) and incubated at 55° C. for 7-14 days. 1 ml of the TSB was plated in tryptone soya agar and incubated at 55° C. for 48-72 hours.

Determination of Carrier Load

The inoculated carrier was placed in 10 ml TSB and sonicated in a 50 Hz ultrasonic bath for 5 minutes. 0.1 ml of the suspension was added to 9.9 ml of TSB to give 1 in 1000 dilution. 1 ml and 0.1 ml of the $10^{-3}$ dilution was plated in tryptone soya agar and incubated at 55° C. for 48-72 hours. The number of colony forming units was determined per carrier.

Determination of $Log_{10}$ Reduction

The number of colony forming units was determined in all plates. The counts were transformed to $log_{10}$ value and the difference between the initial count of the carrier and the number of survivors after treatment was determined. The positive growth in was also determined for each treatment.

Mated Surface Sterilization Test

References herein to a "mated surface sterilization test" are references to a test in which an 85 mm$^2$ mated surface carrier is inoculated, treated, spores if any are recovered and the log 10 reduction in the number of colony forming units resulting from the treatment is reported. (The carrier, inoculation, spore recovery, etc., being as described above)

Simulated Use Testing on Medical Devices—Endoscopes

The purpose of the method is to determine the efficacy of the process on endoscopes under worst case situations. In a number of tests Pentax brand flexible colonoscopes were used. These had lumens ranging in diameter from 1 mm to 4 mm, and lumen lengths ranging from 2.5-3.5 meters. The internal channels of the endoscopes were inoculated with test organism prepared in 5% serum and 340 ppm hard water. A high density of the test inoculum was prepared which allows recovery of >$10^6$ cfu from the lumen prior to initiation of the test. The biopsy, suction and air/water channels were inoculated.

Inoculation of Suction/Biopsy Channels

The test Inoculum was diluted to a level that allowed the recovery of >$10^6$ cfu from the channel prior to initiation of the test. The internal surface of the lumen was inoculated via the suction port with 1 ml test Inoculum, flushed with 50 ml air filled syringe and dried at ambient temperature for 30 minutes.

Inoculation of Air/Water Channels

A high density of the test inoculum was prepared which will allow recovery of >$10^6$ cfu from the lumen prior to initiation of the test. The air and water channels were inoculated with 0.25 ml test Inoculum, flushed with 50 ml air filled syringe and dried at ambient temperature for 30 minutes.

The endoscope was exposed to the process and the survivors were recovered by washing the channels with 100 ml elution fluid (Sterile Distilled Water+0.1 ml catalase) and collected in a sterile container. The collection fluid was mixed thoroughly and filtered through a sterile 0.22 μm membrane filter. The membrane filter was aseptically removed and placed in tryptone soya agar plate and incubated at 55° C. for 2 days.

Determination of Untreated Control

The survivors were recovered by washing the channels with 100 ml elution fluid and collected in a sterile container. The collection fluid was mixed thoroughly and filtered through sterile 0.22 μm membrane filter. The membrane filter was aseptically removed, cut into pieces using a sterile scalpel and transferred into 10 ml TSB ($10^{-1}$ dilution) and Vortexed for 20 seconds. 100 μl of the $10^{-1}$ dilution was further diluted into 9.9 ml TSB to give $10^{-3}$ dilution. 1 ml and 0.1 ml of the $10^{-3}$ dilution was plated in duplicate using tryptone soya agar. The plates were placed into a storage container and incubate plates at 55° C. for 48 hours.

Lumen Sterilization Test

References herein to a "lumen sterilization test" are to a test in which a 1 mm diameter lumen having a length of 2.5 meters is inoculated as specified above for an air channel, treated, survivors if any are determined, and the and the log 10 reduction in the number of colony forming units resulting from the treatment is reported.

Example 1

35% hydrogen peroxide was nebulised in the apparatus previously described with reference to FIG. 2 and with the sterilization chamber on line. Unless otherwise specified the system parameters used in all examples were:

Nebulized solution: hydrogen peroxide in water.
Feed peroxide conc.: 35 wt %.
System volume: 0.04 m$^3$.
Nebuliser delivery rate: 8+/−1.5 mg/min
Nebuliser duty cycle: 20 sec/min
Power supply; 27+/−2 mg/min
Aerosol flow rate: 1.5+/−0.3 m/s
Initial chamber humidity 20% RH
Chamber temperature: 45° C.

Figure 1:
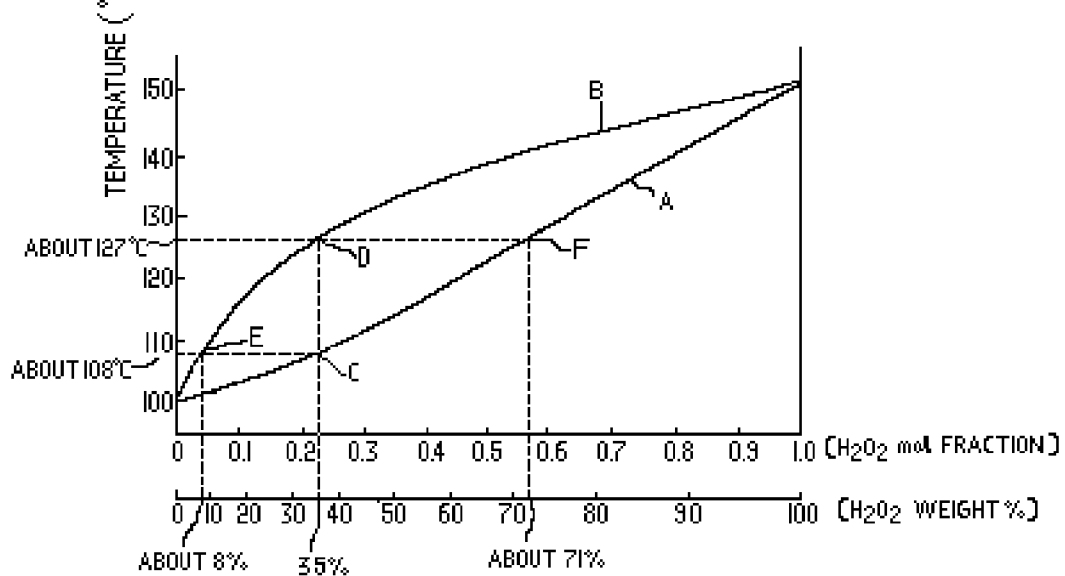
FIG. 1 is a reproduction of a figure from U.S. Pat. No. 4,797,255 which shows (curve A) how the boiling point of a water/peroxide mixture changes with concentration at atmospheric pressure and (curve B) how the gas composition changes.

In example 1 the system parameters were as described above, except that the nebuliser delivery rate was 10 mg/l/min and the applied energy in heater 17 was 1.5 KJ/min. Water removal was by means of a cold trap 17 utilizing a Peltier device to achieve cooling. The nebulant issued from the cold trap from outlet 23 at a temperature of 45° C. Appended Table 2 and FIG. 9 show the relative humidity in the chamber of FIG. 1 over a 15 minute cycle.

Figure 9:
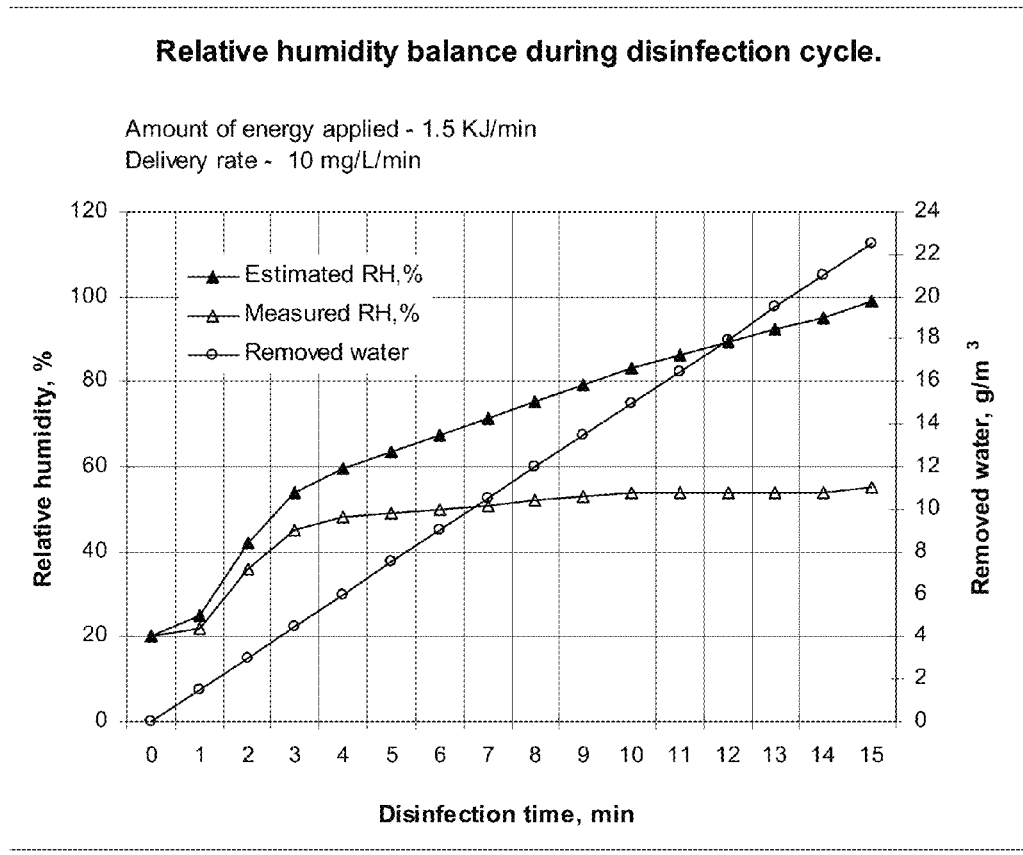
FIG. 9 is a graph showing how relative humidity changes over a disinfection cycle in one embodiment of apparatus according to the invention

As shown in FIG. 9 the relative humidity rose to above 40% in 2-3 minutes and thereafter remained between 40% and about 55%. Approximately 22.5 g/m$^3$ of water were removed from the system during the cycle. In the absence of water removal the relative humidity in the chamber the relative humidity would have risen to above 60% within 4 minutes, would reach 80% in about 9 mins and would be above 95% by the end of the cycle.

In this experiment the article to be sterilized was exposed to the nano-nebulant dynamically—that is to say during the whole of the cycle. In those circumstances it will be disinfected more rapidly than if the system is first brought to equilibrium and the article is then exposed under static conditions to the nano-nebulant for a period.

Example 2

Figure 10:
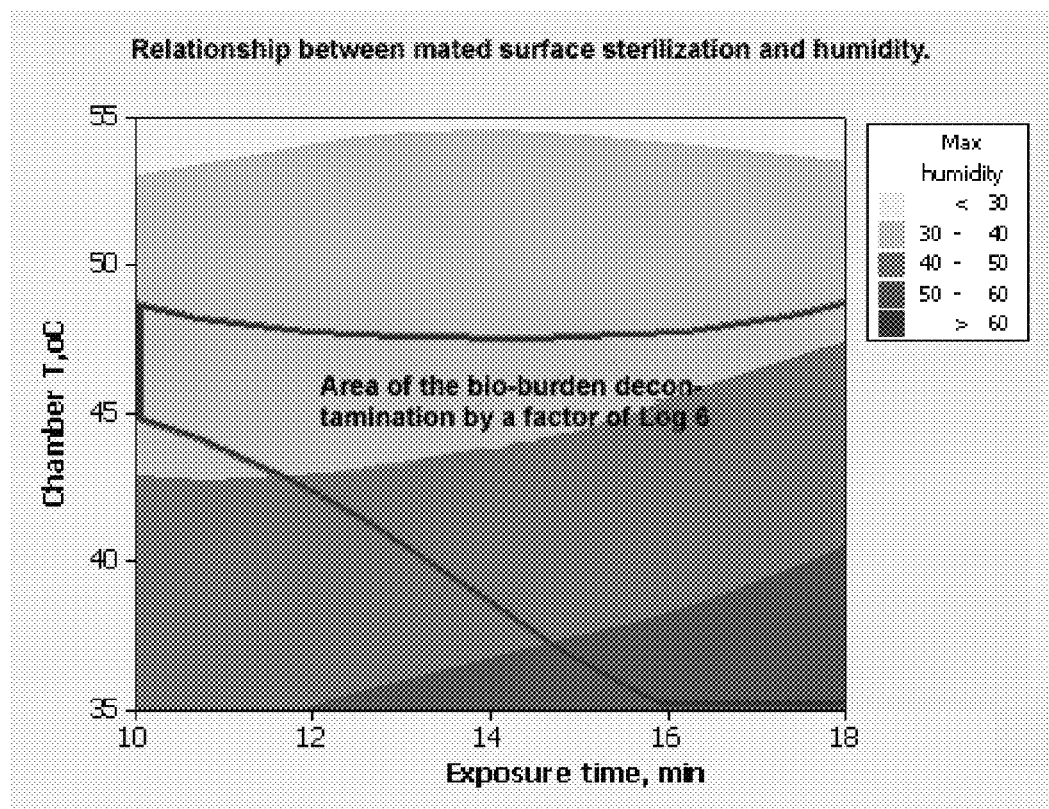
FIG. 10 is a diagram showing the boundary conditions of temperature, exposure time and relative humidity to obtain sterilization.

A number of experiments were performed with mated surfaces according to the mated surface test previously described being placed in sterilization chamber 1. using the embodiment of FIG. 2. The parameters were generally as for example 1, except that temperature, relative humidity, and exposure time were varied. Appended FIG. 10 shows the boundary conditions of RH % and temperature required to obtain a log 6 reduction in a bio burden on mated surfaces using the mated surface test and within a given time. A log 6 reduction in bio burden was obtained within the area indicated in FIG. 10. Outside that area, the log reduction was less than 6. Thus mated surfaces could be sterilized in 10 minutes at between 45 and 48° C. and at 30-40% RH, and in 14 minutes from about 36° C. to 47.5° C. and at a relative humidity of between 30% and 60% RH. Although not shown in FIG. 10, it is noteworthy that a log 6 reduction is not achievable within 20 minutes at greater than about 70%-80% RH and temperatures below 70° C. at atmospheric pressure.

Example 3

In this example a variety of different endoscopes were sterilized according to the invention over a 10 minute sterilization period. The endoscopes were inoculated as previously described and then placed in a sterilization chamber 1 of apparatus according to FIG. 2. The apparatus was controlled and operated in accordance with the invention, the parameters being as in example 1 except as specified. Under the equilibrium conditions tabulated, the nano-mist was admitted to the sterilization chamber for 10 minutes, and the microbiological efficacy of the treatment was then measured. The results are reported in appended table 3. It can be seen that the treatment was effective in sterilizing lumens ranging from 1 mm to 4 mm in diameter and up to 3.5 m in length within 10 minutes.

By way of comparison, a prior art nebulant of 35% hydrogen peroxide at 43° C. and at 100% humidity (no water removal), while able to achieve sterilization in a 1 mm diameter lumen of 2.5 meters length in under 30 mins, did so with so much deposition of peroxide solution on the surface that requirements for peroxide removal and drying extended the cycle time to periods in excess of 60 minutes which were commercially impractical.

Example 4

In this example mated surface assemblies comprising stainless steel washers with flat surfaces directly in apposition (85 mm$^2$ mated surface) were inoculated as previously described. The mated surface assemblies were placed in a sterilization chamber of apparatus according to FIG. 2. The apparatus was controlled and operated in accordance with the invention, with operating parameters as described for example 1 except as indicated in table 4. Under the equilibrium conditions tabulated, the nano-mist was admitted to the sterilization chamber for 10 or 15 minutes, and the microbiological efficacy of the treatment was then measured. The results in appended Table 4 show that sterilization of mated surfaces can be obtained very reliably in 10 minutes.

Example 5

The experiment of example 4 was repeated using mated surface assemblies of increasing mated surface area up to 450 mm$^2$. The results are reported in appended table 5 showing that the method is also effective on larger mated areas.

Example 6

Example 4 was repeated with open (as distinct from mated) surfaces but in wet, dry, and freshly inoculated condition. The results are given in appended table 6 and show that on an open exposed surface, a log 6 reduction in bio burden can be achieved within 3 minutes in each case.

Example 7

In this example a sterilization process according to the invention was applied to surfaces of different material composition by the method of the invention as in previous examples. The samples tested were open surfaces of 20×20 mm area. The results are given in appended table 7 which shows that, on an open exposed surface, a log 6 reduction in bio burden can be achieved within 3 minutes for most materials, but that 5 mins is required on silicone and neoprene rubber, and 10 mins was required on polyurethane and nylon. 10 minutes was required for stainless steel and pennicylinders The system parameters were as in example 1, except as specified.

It is noteworthy that sterilization of stainless steel open surfaces was obtainable at 25° C. under the conditions shown.

Example 8

This example shows the advantages of a method employing steps 2 and 3 of the invention (i.e. a heating step in combination with a water removal step) in an aerosol process.

In table 5 of our earlier application (Kritzler et al, PCT/AU99/00505) obtained a 6 log reduction of spores—in that case *B. subtillis* which is much easier to kill than *B. stearothermophilus* (ATCC 7953)—with 1% peroxide in 60 secs on an open surface. At the end of 60 secs, there were aprox. 50 mg of peroxide on the glass plates used (5 mg/cm$^2$).

In Example 8, experiment A was repeated but using *B. stearothermophilus* and 10% peroxide. Sterilization using the mated surface sterilization test required longer than 60 minutes. The weight of peroxide on an open surface was measured after 60 seconds as shown in appended Table 8. In other prior art, a peroxide nebulant has been heated. In experiment B, a 35% peroxide nebulant was circulated in apparatus according to FIG. 1 and heated to 40° C., without removal of water, prior to the samples being exposed to the nebulant. In experiment C the sample was both heated to 40° C. and water was removed in accordance with the invention. Experiment C was the same as experiment B except that water vapour was removed in experiment C until the peroxide concentration would have exceeded 60% in the droplets, and the relative humidity was 55%. In experiment D a 60% peroxide solution was nebulized and heated, but no water was removed.

While all experiments identified in table 8 achieved sterilization within 1 min on exposed open surfaces, the process of the invention (experiment C) used significantly less peroxide, and resulted in a greatly reduced residual amount on the surface. This is significant in reducing drying time, cytotoxic risk, and is significantly more economical. Furthermore, experiment C according to the invention achieved significantly faster treatment on mated surfaces than experiments A, B, or D. These results show that the benefits of the invention are not simply attributable to increase in peroxide concentration.

Example 9

In this example the efficacy of the nano nebulant prepared according to the invention was compared with a peroxide vapour under the same conditions. Two identical sets of carriers were placed in the sterilization chamber of FIG. 2 which was operated as previously described in accordance with the invention. Each set had inoculated penicylinders and inoculated mated stainless steel washers. One set was placed inside a TYVEK™ bag inside sterilization chamber 1, while the other set was outside the TYVEK™ bag but inside the chamber. The set within the bag was thus exposed to hydrogen peroxide vapour but was not accessible to the nano nebulant mist which does not penetrate TYVEK™. The time of exposure was 2 minutes. As shown in appended table 9 in which the nano nebulant is described as "mist", the nano nebulant was far more effective than the vapour alone.

Example 10

Table 10 (and corresponding FIGS. 11, 12, 13 &14) show log reduction in bio-burden for mated surfaces under various conditions of operation of apparatus according to FIG. 2.

FIG. 11 shows that aerosol flow velocity should be chosen to provide a peroxide delivery rate above about 8 mg/L/min at a temperature of 45° C. and a relative humidity in the range of 40-50% in apparatus according to FIG. 2 to achieve a log 6 reduction in spores in 10 minutes.

Figure 13:
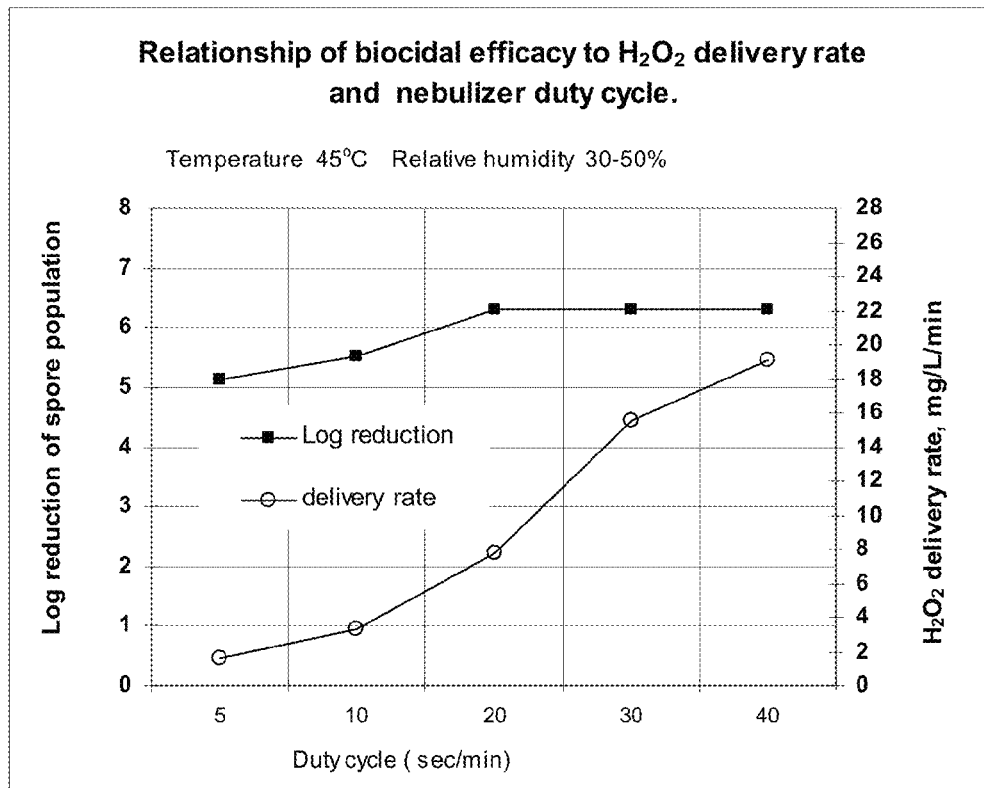
FIG. 13 is a graph showing a relationship between biocidal efficacy and peroxide delivery rate, and nebuliser duty cycle.

FIGS. 12 and 13 show that the nebulization conditions can be selected over a range of suitable power outputs and duty cycles to obtain a sufficient delivery rate. Surprisingly it was found that differing duty cycles had relatively little effect on the degree of sterilization in a given time but a significant effect on drying time and peroxide residuals. Table 11 shows the results for runs using a cassette similar to that in FIG. 8A containing a probe to be sterilized. The cassette was placed inside chamber 1. and subjected to differing nebuliser duty cycles. The final relative humidity in the cassette was significantly different for the differing nebuliser duty cycles, but the reduction in bioburden was substantially constant.

The hydrogen peroxide vapour concentration in equilibrium with the nebulant in the chamber also differed as one would expect from the resulting differing density of hydrogen peroxide in the cassette when sealed.

Figure 14:
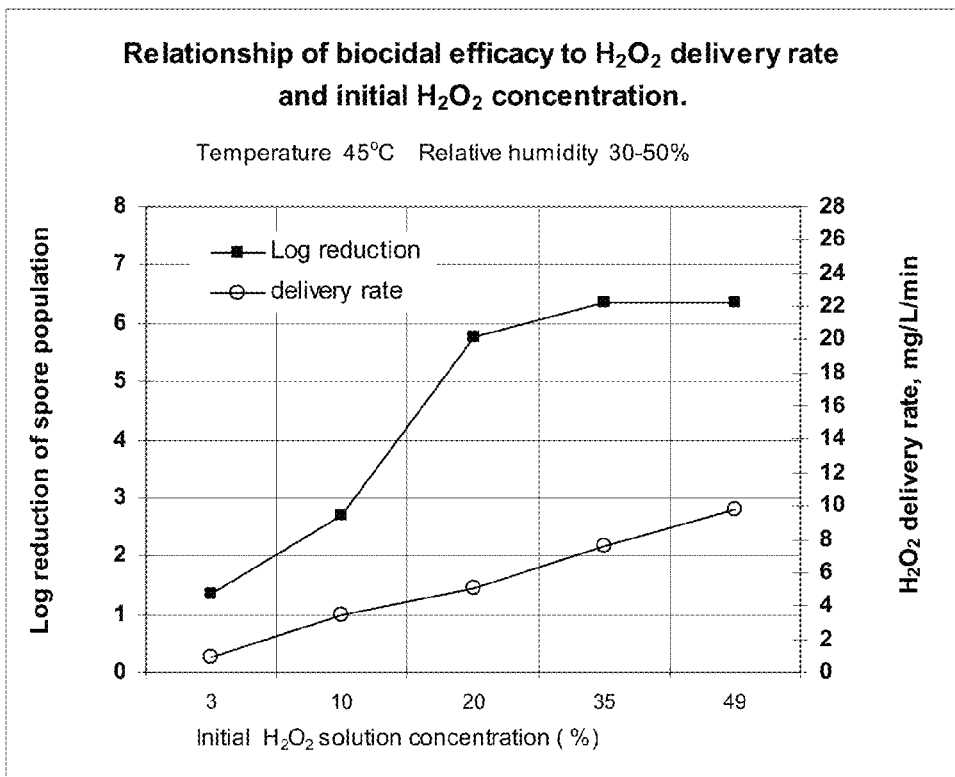
FIG. 14 is a graph showing a relationship between biocidal efficacy and peroxide delivery rate, and initial peroxide concentration.

FIG. 14 shows that for the parameters discussed an initial peroxide solution concentration of down to about 30% is satisfactory for sterilization at 45° C. and 30-60% RH. However concentrations down to 6% and perhaps 1% can be used if longer times can be tolerated or efficiency otherwise improved.

It appears that in a 27.5 Liter chamber optimum conditions to achieve sterilization in between 5-20 minutes involve a delivery rate of around 7 mg/l/min or more of peroxide at an initial concentration of from 25%-30% and at a chamber temperature of about 45° C.+/−3. with water removal at a rate to maintain the humidity at below 60%. The optimum parameters for differing design of chamber can readily be determined by those skilled in the art based on the teaching herein.

Example 11

Figure 15:
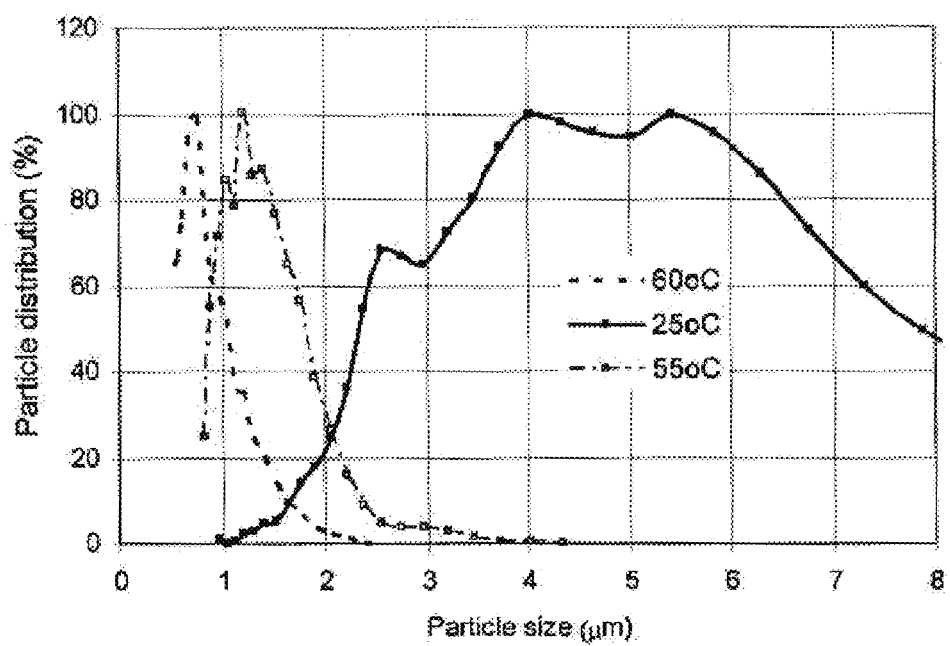
FIG. 15 is a graph showing how particle size distribution changes with temperature during step (2) of the method of the invention.

In the embodiment described with reference to FIG. 2, the particles exiting nebulizer 5 at nebuliser outlet 8 ordinarily have an average particle size of about 5 microns at ambient temperature. As seen in FIG. 15 the particle size distribution of particles exiting the nebuliser (i.e. in the absence of heat) have a broad distribution extending from diameters around 1 micron up to above 8 microns, but with most particle diameters being in the 3-7 micron range. The particle sizes were then estimated in an experiment which simulated the particle size at heat exchanger outlet 18, with heater 17 operating at differing energy inputs. When the nebulant is heated to 60° C., the particle size distribution peaks at about 0.8 microns and about half of the particles have a diameter smaller than 0.8 microns. The diffusion coefficient of aerosol particles increases exponentially at below about 1 micron. It is believed that if water is not removed from the system, the particles will re-equilibrate with water and return to their original size in a short time. The measurements were made with a "Malvern Mastersizer 2000", from Malvern Instruments, Malvern, UK which has a lower detection limit of 0.5 microns.

In summary it can be seen that the invention provides an economical and relatively simple solution to the problems of sterilizing medical instruments, including heat sensitive endoscopes and the like. It does not require a vacuum system and it does not require a washing system to remove sterilant. It does not require the use of highly concentrated hydrogen peroxide as a starting material but can achieve sterilization within 20 minutes starting from a relatively safe to handle 35% concentration of solution.

The examples discussed show that sterilization (6 log reduction in bio-contamination) can in fact be achieved within 15 minutes, at atmospheric pressure, over a wide range of operating conditions, with both lumens and mated surfaces.

For a 27.5 liter sterilization chamber, optimum results were obtained with a peroxide concentration in the range of 25% to 35% in the nebuliser, a concentration in the nano particles of at least 60%, a temperature in the chamber of 45 C.° plus/minus 3 C.° and a sterilization cycle time of between 5 and 20 minutes at humidities in the range 30-60% and preferably above 40% RH.

The inventors have found that concentrations of biocide which may be introduced into a chamber as a nano-nebulant can be as high as 11.7 g/liter. That can be compared with maximums achievable for vapour systems (in the absence of evacuation) of 0.9 mg/l at 25° C. and 40% RH (even less at higher temperatures or humidity) and rising to 2.0 mg/l at 0% humidity or 14.4 mg/l at 60° C. and 10% RH.

The data of example 10 demonstrates that the efficacy is not due to the presence of peroxide vapour.

Although the invention has been described in the context of apparatus for sterilizing medical instruments and in relation to a sterilization chamber it will be understood that the same principles can be applied to disinfection of chambers and ducts of all sizes. It will be understood that the invention is suitable for sterilizing an operating theatre room, a silo or other large volume chambers. In those cases the nebulizer system, heating system and water vapour removal system, will need to be scaled up to an appropriate extent and appropriate monitoring and control systems employed, but since no vacuum is required and the concentrations of aerosol are not excessive, there are no special difficulties in scaling up the process. Sufficient water vapour removal can be accomplished with available air-conditioning systems.

It is not clear why the method of the invention is so much more efficient than vapour systems. It is thought that as water molecules are lighter and diffuse faster than peroxide vapour molecules, they tend to block passage of peroxide vapour molecules into lumens and crevices. The nano nebulant particles on the other hand are heavy in comparison with water molecules and have much greater momentum. Also the nano particles possibly have a longer residence time on surfaces on which they impinge than vapour molecules. Certainly the fact that much higher densities of peroxide in the form of nano particles in an aerosol can be provided in a given volume than is obtainable with vapour may be a factor. In comparison with prior nebulant systems, the invention provides an ability to penetrate mated surfaces and lumens which has not previously been attainable and does so with an order of magnitude less residue on the surface of the treated article.

As will be understood by those skilled in the art from the teaching hereof the invention may be embodied in many forms. The method and apparatus may be performed by combining a variety of different unit operations in combination to perform the novel method described. A person skilled in the art could further optimise the process based on the inventive principles herein disclosed, without departing from the scope hereof.

What is claimed is:

1. A method for disinfecting or sterilizing a surface comprising the steps of:
   (1) nebulising a solution comprising a sterilizing agent in a solvent to form a nebulant of finely divided particles of the solution in a gas stream, said solution including a solvent having a lower boiling point than the sterilizing agent;
   (2) subjecting the nebulant to energy of a kind and for a duration sufficient to vaporize solvent in preference to sterilizing agent to increase the concentration of the sterilizing agent in the nebulant particles;
   (3) removing solvent vaporized in step (2) from the gas stream at or above atmospheric pressure and, optionally cooling the nebulant to below 70° C.; and
   (4) exposing said surface to the nebulant of concentrated sterilizing agent from step (3) for a time sufficient to disinfect or sterilize the surface.

2. A method according to claim 1 wherein steps (1) to (4) are conducted at atmospheric pressure or above.

3. A method according to claim 2 wherein the surface is a mated surface or a lumen and wherein a 6 log reduction in micro-organism load in a mated surface sterilization test or a lumen sterilization test is achieved within 20 minutes exposure time to the nebulant from step (3) at atmospheric pressure.

4. A method according to claim 3 wherein a 6 log reduction in micro-organism load in a mated surface sterilization test is achieved within 10 minutes exposure time to the nebulant from step (3) at atmospheric pressure.

5. A method according to claim 1 wherein the sterilizing agent is selected from the group consisting of hydrogen peroxide, peracetic acid, and mixtures thereof.

6. A method according to claim 1 wherein the solvent is, or includes, water.

7. A method according to claim 6 wherein the solution in step (1) is 35% or less hydrogen peroxide in water.

8. A method according to claim 7 wherein water vapour is removed from the gas stream at or above atmospheric pressure in step (3) by a cold trap or condenser, a molecular sieve or desiccant, a semipermeable membrane device, or other water removal means operable at or above atmospheric pressure, while leaving the particles of concentrated peroxide solution in suspension in the gas stream.

9. A method according to claim 6 wherein step (2) includes heating the nebulant.

10. A method according to claim 9 wherein the nebulant is heated during passage over a heating element, which transfers sufficient energy to the solution particles to vaporize water therefrom.

11. A method according to claim 1 wherein the nebulising of step (1) is conducted with an ultrasonic transducer.

12. A method according to claim 1 wherein in step (3), the sterilizing agent concentration in the nebulant increases to 60% to 80% while the particles shrink to an average diameter of less than 1 micron.

13. A method according to claim 12 wherein the particles shrink to an average diameter of less than 0.8 micron.

14. A method according to claim 1 wherein the surface is exposed to nebulant from step (3) for a time sufficient to sterilize the surface.

15. Apparatus for disinfecting or sterilizing a surface comprising:
   (1) means adapted to produce a nebulant comprising finely divided particles of a solution suspended in a gas, the solution comprising a solute and a solvent;
   (2) means for supplying sufficient energy to the nebulant to selectively flash off at least some of the solvent as a vapour, whereby the concentration of solute in nebulant particles is increased;
   (3) means to separate solvent vapour from the nebulant after at atmospheric pressure, and optionally means for cooling the nebulant to below 70° C.; and
   (4) means for exposing the surface to be disinfected or sterilized to the nebulant obtained from the solvent vapour separation means (3).

16. Apparatus according to claim 15 further comprising means for controlling the energy supplied to the nebulant, to ensure that solvent is vaporised in preference to solute.

17. Apparatus according to claim 16 wherein the means for nebulization are selected from the group comprising ultrasonic nebulizers, sprays, jet nebulizers and piezoelectric nebulizers, operated continuously or cyclically.

18. Apparatus according to claim 17 wherein the nebulizers are switched on and off cyclically.

19. Apparatus according to claim 16 wherein the means for supplying sufficient energy to the nebulant is by means selected from a heating element; infrared, laser, microwave, RF or other radiation generating means;

induction heating means; heat exchanger; conduction means; convection means; and mechanical energy transfer means.

20. Apparatus according to claim 15 wherein the step of vapour removal is carried out by means selected from means for passing the gas through a drying agent, desiccant, or through suitable molecular sieves, membranes, means for passage through a centrifuge, and means of a suitable cyclonic separator.

* * * * *

UNITED STATES PATENT AND TRADEMARK OFFICE
CERTIFICATE OF CORRECTION

| | | |
|---|---|---|
| PATENT NO. | : 9,241,491 B2 | Page 1 of 1 |
| APPLICATION NO. | : 14/085924 | |
| DATED | : January 26, 2016 | |
| INVENTOR(S) | : Vladimir Berentsveig, Gary Erickson and Ron Weinberger | |

It is certified that error appears in the above-identified patent and that said Letters Patent is hereby corrected as shown below:

In the Claims:

Column 26, Claim 15, Line 22 "after at atmospheric pressure,..."

should read --at atmospheric pressure,--

Signed and Sealed this
Twenty-fourth Day of May, 2016

Michelle K. Lee
*Director of the United States Patent and Trademark Office*